(12) United States Patent
Sanhaji et al.

(10) Patent No.: US 10,844,412 B2
(45) Date of Patent: Nov. 24, 2020

(54) SOLID FORM OF (−)-AMBROX FORMED BY A BIOCONVERSION OF HOMOFARNESOL IN THE PRESENCE OF A BIOCATALYST

(71) Applicant: Givaudan SA, Vernier (CH)

(72) Inventors: Ghislain Sanhaji, Warmeriville (FR); Alix Rousseaux, Verzenay (FR); Sandrine Noel, Warmeriville (FR); Eric Eichhorn, Zurich (CH)

(73) Assignee: Givaudan S. A., Vernier (CH)

( * ) Notice: Subject to any disclaimer, the term of this patent is extended or adjusted under 35 U.S.C. 154(b) by 0 days.

(21) Appl. No.: 16/095,444

(22) PCT Filed: Apr. 20, 2017

(86) PCT No.: PCT/EP2017/059327
§ 371 (c)(1),
(2) Date: Oct. 22, 2018

(87) PCT Pub. No.: WO2017/182542
PCT Pub. Date: Oct. 26, 2017

(65) Prior Publication Data
US 2019/0136275 A1 May 9, 2019

(30) Foreign Application Priority Data

Apr. 22, 2016 (WO) .................. PCT/EP2016/058987
Apr. 22, 2016 (WO) .................. PCT/EP2016/058997
Oct. 26, 2016 (GB) .................................. 1618090.3

(51) Int. Cl.
C07D 307/92 (2006.01)
C12P 17/04 (2006.01)
A61Q 13/00 (2006.01)

(52) U.S. Cl.
CPC .............. *C12P 17/04* (2013.01); *A61Q 13/00* (2013.01); *C07D 307/92* (2013.01); *C07B 2200/07* (2013.01); *C07B 2200/13* (2013.01); *C12Y 504/99017* (2013.01)

(58) Field of Classification Search
CPC ....... C12P 17/04; A61Q 13/00; C07D 307/92; C07B 2200/07; C07B 2200/13; C12Y 504/99017
USPC ........................................................ 549/458
See application file for complete search history.

(56) References Cited

U.S. PATENT DOCUMENTS

| | | |
|---|---|---|
| 6,524,831 B2 | 2/2003 | Steinbüchel et al. |
| 8,759,043 B2 | 6/2014 | Breuer et al. |
| 8,932,839 B2 | 1/2015 | Breuer et al. |
| 9,493,385 B2 | 11/2016 | Weingarten et al. |
| 2003/0092143 A1 | 5/2003 | Rabenhorst et al. |

(Continued)

FOREIGN PATENT DOCUMENTS

| | | |
|---|---|---|
| CN | 105 037 308 A | 11/2015 |
| EP | 2 438 182 A2 | 12/2010 |

(Continued)

OTHER PUBLICATIONS

PCT/EP2017/059327—International Search Report, dated Jun. 29, 2017.

(Continued)

*Primary Examiner* — Taylor V Oh
(74) *Attorney, Agent, or Firm* — Curatolo Sidoti Co., LPA; Salvatore A. Sidoti; Floyd Trillis, III

(57) ABSTRACT

A solid form of (−)-Ambrox formed by a bioconversion process.

9 Claims, 4 Drawing Sheets

Specification includes a Sequence Listing.

(56) References Cited

U.S. PATENT DOCUMENTS

| | | |
|---|---|---|
| 2009/0117557 A1 | 5/2009 | Wang et al. |
| 2012/0135477 A1 | 5/2012 | Breuer et al. |
| 2012/0237991 A1 | 9/2012 | Breuer et al. |
| 2013/0273619 A1 | 10/2013 | Bonnekessel et al. |
| 2016/0304911 A1 | 10/2016 | Sato et al. |
| 2018/0134678 A1 | 5/2018 | Eichhorn |
| 2018/0148751 A1 | 5/2018 | Eichhorn et al. |

FOREIGN PATENT DOCUMENTS

| | | |
|---|---|---|
| JP | 2009-60799 A | 3/2009 |
| JP | 2013-132226 A | 7/2013 |
| JP | 2017-074053 A | 4/2017 |
| WO | WO 2004/063699 A2 | 7/2004 |
| WO | WO 2010/139710 A1 | 12/2010 |
| WO | WO 2012/066059 A2 | 5/2012 |
| WO | WO 2015/033746 A1 | 3/2015 |
| WO | WO 2015/059290 A1 | 4/2015 |
| WO | WO 2015/059293 A1 | 4/2015 |
| WO | WO 2016/170099 A1 | 10/2016 |
| WO | WO 2016/170106 A1 | 10/2016 |
| WO | WO 2017/068401 A1 | 4/2017 |

OTHER PUBLICATIONS

PCT/EP2017/059327—International Written Opinion, dated Jun. 29, 2017.
PCT/EP2016/058987—International Search Report, dated Jun. 8, 2016.
PCT/EP2016/058987—International Written Opinion, dated Jun. 8, 2016.
PCT/EP2016/058997—International Search Report, dated Jun. 22, 2016.
PCT/EP2016/058997—International Written Opinion, dated Jun. 22, 2016.
Great Britain Search Report GB 1618090.3, dated Aug. 31, 2017.
Decorzant, et al., "A Short Synthesis of Ambrox® from Sclareol", Tetrahedron, Jan. 1, 1987, vol. 43, No. 8, pp. 1871-1879, Elsevier Science Publishers, Amsterdam, Netherlands.
Barrero, et al., "Degradation of the Side Chain of (−)-Sclareol: A Very Short Synthesis of nor-Ambreinolide and Ambrox", Synthetic Communications, 2004, vol. 34, No. 19, pp. 3631-3643, Marcel Dekker, Inc.
Moulines, et al., "A Practical Synthesis of Ambrox® From Sclareol Using No Metallic Oxidant", Synthetic Communications, 2001, vol. 31, No. 5, pp. 749-758, Marcel Dekker, Inc.
Castro, et al., "Sythesis of Ambrox® from Labdanolic Acid", Tetrahedron, 2002, vol. 58, No. 29 pp. 5941-5949.
Mori, et al., "Synthesis of Ambrein and Ambrox®", Liebigs Ann. Chem., 1990, pp. 361-368.
Barrero, et al. "Synthesis of Ambrox® from (−)-sclareol and (+)-cis-abienol", Tetrahedron, 1993, vol. 49, No.45, pp. 10405-10412.
Bolster, et al. "The Synthesis of (−)-Ambrox® Starting From labdanolic Acid", Tetrahedron, 2001, vol. 57, No. 26, pp. 5657-5662.
Seitz et al., "Substrate specificity of a novel squalene-hopene cyclase from Zymomonas mobilis", J. Molecular Catalysis B: Enzymatic, Dec. 2012, vol. 84, pp. 72-77. (Only Abstract provided).
Broun et al., "Catalytic plasticity of fatty acid modification enzymes underlying chemical diversity of plant lipids", Science, 1998, vol. 282: 1315-1317.
Devos et al., "Practical limits of function prediction", Proteins: Structure, Function, and Genetics. 2000, vol. 41: 98-107.
Seffernick et al., "Melamine deaminase and Atrazine chlorohydrolase: 98 percent identical but functionally different", J. Bacterial., 2001, vol. 183 (8): 2405-2410.
Seitz VM., Ph.D., Dissertation thesis, 2013, pp. 1-176.
Siedenburg et al., "Minireview: Squalene-Hopene cyclases", Appl. Environ. Micrbiol., 2011, vol. 77(12): 3905-3915.
Whisstock et al., "Prediction of protein function from protein sequence", Q. Rev. Biophysics., 2003, vol. 36 (3): 307-340.
Witkowski et al., "Conversion of b-ketoacyl synthase to a Malonyl Decarboxylase by replacement of the active cysteine with glutamine", Biochemistry, 1999, vol. 38: 11643-11650.
Leffingwell, et al., "Biotechnology-Conquests and Challenges in Flavors and Fragrances", Leffingwell Reports, Mar. 1, 2015, vol. 7, No. 2, pp. 1-11.
Escher et al, "Configuration -Odor Relationships in 5 beta-Ambrox", Helvetica Chimica Acta, 1990, vol. 73, p. 1935-1947.

SOLID FORM OF (−)-AMBROX FORMED BY A BIOCONVERSION OF HOMOFARNESOL IN THE PRESENCE OF A BIOCATALYST

CROSS REFERENCE TO RELATED APPLICATIONS

This application is a national stage application of International Application No. PCT/EP2017/059327, filed 20 Apr. 2017, which claims priority from Great Britain Patent Application No. 1618090.3, filed 26 Oct. 2016, PCT Application No. PCT/EP2016/058997, filed 22 Apr. 2016, and PCT Application No. PCT/EP2016/058987, filed 22 Apr. 2016, which applications are incorporated herein by reference.

FIELD OF THE INVENTION

The present invention is concerned with a solid form of (−)-Ambrox, as well as methods of preparing and purifying same.

BACKGROUND OF THE INVENTION

AMBROFIX™ is the proprietary Givaudan trade name of its (−)-Ambrox having the general formula (I)

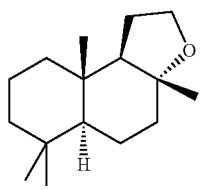

(I)

AMBROFIX™ is a very important molecule in the perfumers' palette of ingredients. It delivers a highly powerful, highly substantive and highly stable ambery note for use in all perfumery applications. AMBROFIX™, available from Givaudan, is the most suitable material for obtaining an authentic ambergris odour note.

Currently AMBROFIX™, as is the case with other commercial forms of (−)-Ambrox, is produced by synthetic chemistry from starting materials of natural origin. The availability and quality of certain starting materials are dependent on climatic conditions, as well as socioeconomic factors. Furthermore, since starting materials may be extracted from natural resources, with modest yields, they are available at prices that will, in all likelihood, increasingly render their use uneconomical on an industrial scale. Accordingly, if commercial industrial supplies of AMBROFIX™ are to continue to be available at a reasonable cost, there is a need for a more cost-effective process of production and purification, which is capable of industrialization.

An industrially scalable biotechnological route into (−)-Ambrox would be attractive because it is potentially less complex, greener and more environmentally friendly than fully synthetic chemistry procedures.

A potentially useful substrate on which to attempt a bioconversion to provide (−)-Ambrox is homofarnesol. In their seminal paper, Neumann et al (Biol. Chem. Hoppe-Seyler Vol. 367 pp 723-726 (1986)) discussed the feasibility of converting homofarnesol to (−)-Ambrox under enzymatic catalysis, employing the enzyme Squalene Hopene Cyclase (SHC). The homofarnesol employed was a mixture of the four geometric isomers of this molecule. Of the four isomers, only the 7E,3E geometric isomer (using conventional nomenclature) could be cyclized, and then only with very low yield of the desired (−)-Ambrox.

JP 2009-60799 (Kao) discloses a synthesis whereby SHC acts on a homofarnesol substrate to produce (−)-Ambrox. The substrate is a mixture of all four geometric isomers (3Z,7Z; 3E,7Z; 3Z,7E; and 3E,7E). The document only discloses the preparation of (−)-Ambrox from homofarnesol using liquid extracts containing SHC prepared from a recombinant micro-organism expressing the SHC gene. The homofarnesol mixture is converted to (−)-Ambrox and its 9-epi stereoisomer, and purification can be carried out by distillation or by column chromatography. Kao does not describe a process whereby homofarnesol is converted into (−)-Ambrox using substantially whole or intact microorganisms producing SHC, and furthermore, it does not provide any technical teaching related to the downstream processing of complex reaction mixtures obtained by such processes that can yield (−)-Ambrox in olfactively pure form.

To the applicant's knowledge, the prior art does not describe any viable, industrially scalable processes, involving the SHC-catalyzed bioconversion of homofarnesol, to provide (−)-Ambrox in olfactively pure form.

Furthermore, if bioconversion of homofarnesol is to be realized on an industrial scale, cost-efficient sources of highly pure, 3E,7E-homofarnesol should be available. However, although synthetic routes into homofarnesol have been described in the literature (see for example US 2013/0273619), to the applicant's knowledge there are no cost-effective, industrial-scale sources of pure 7E,3E-homofarnesol currently available.

There remains a need to provide an economically feasible and industrially scalable route into the valuable fragrance ingredient (−)-Ambrox.

In co-pending patent applications PCT/EP2014/072891 (published as WO 2015/059293) and PCT/EP2014/072882 (published as WO 2015/059290), the applicant describes an efficient method of preparing 7E,3E/Z-homofarnesol mixture that is enriched in the 7E,3E geometric isomer. The 7E,3E/Z-homofarnesol mixture is prepared from beta-farnesene, and the isomeric information contained in this starting material is preserved, such that the homofarnesol double bond at the 7-position is fixed in the E-configuration. However, even this elegant chemistry still results in a 3E/Z isomer mixture. Pure 7E,3E-homofarnesol remains synthetically challenging, and might only be achieved by means of economically disadvantageous purification of isomeric mixtures.

Despite developments related to the biocatalytic production of (−)-Ambrox from homo-farnesol, there remains a need to provide efficient means of separating and purifying (−)-Ambrox from bioconversion media containing particulate material and other material, for example cell debris, as well as possible by-products, unreacted substrate, and any solvents or other reagents employed in the bioconversion process.

SUMMARY OF THE INVENTION

In addressing the deficiencies in the prior art, the applicant surprisingly found that a crystalline form of (−)-Ambrox can be formed in a biocatalytic process. More particularly, the applicant found that crystals of (−)-Ambrox form in the bioconversion medium.

The surprising and unexpected manner in which (−)-Ambrox crystallizes in a bioconversion medium, as well as the physical characteristics of the crystals that are formed is particularly relevant in terms of the isolation and purification from a bioconversion medium, of an essentially colourless and olfactively pure form of (−)-Ambrox exhibiting an authentic ambergris odour note. In the event that the biocatalyst is a microbial biocatalyst, then the finding that (−)-Ambrox obtained in an olfactively pure quality is particularly surprising in view of the fact that microbial biocatalysts present in the bioconversion medium can have extremely unpleasant and even offensive off-note characteristics. The surprising finding that crystals of (−)-Ambrox are formed external of the microbial catalysts in a bioconversion medium enables particularly efficient separation of (−)-Ambrox from a foul-smelling medium.

Accordingly, the invention provides in a first aspect a solid form of the compound of the formula (I)

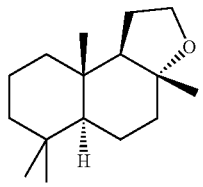

(I)

wherein said solid form is characterized by at least one of the following characteristics:— it exhibits a powder x-ray diffraction pattern having at least one of the following peaks at diffraction angles 2 theta of about 15.6, 16.2, 16.7, 17.0, 17.4, 18.3+/−0.20;

it comprises elongate crystals having an average diameter of between 10 to 400 microns, more particularly 40 to 400, and more particularly still 100 to 400 measured by laser granulometry;

it comprises elongate crystals having a length measured along their longest dimension of 20 to 600 microns, more particularly 40 to 500, and more particularly still 100 to 400, preferably of greater than 100, more particularly greater than 200, and more particularly still greater than 300 microns, measured by laser granulometry; and it is substantially colourless, as that term is defined, herein below.

In a more particular embodiment, the solid form of the compound of the formula (I) is characterized by a powder x-ray diffraction pattern exhibiting the following peaks at diffraction angles 2 theta of about 15.6, 16.2, 16.7, 17.0, 17.4 and 18.3+/−0.20.

In a still more particular embodiment, the solid form of the compound of the formula (I) is characterized by a powder x-ray diffraction pattern substantially as depicted in FIG. 1, below.

A solid form of (−)-Ambrox formed by a biocatalytic process has neither been described nor suggested hitherto in the prior art, to the best knowledge of the applicant.

Accordingly, the invention provides in another of its aspects a solid form of a bioconversion product according to the formula (I).

In an embodiment of the invention, the solid form of a bioconversion product according to the formula (I) has at least one of the characterizing features referred to herein above.

The powder x-ray diffraction data referred to above can be collected in a straightforward manner using diffractometer equipment well known in the art. Methodology and instrumentation used to measure powder x-ray diffraction patterns referred to herein are described in more detail in the Examples.

The shape of the crystals was determined by microscopy according to methods well known in the art, and which require no further elaboration here.

The characteristic size and shape of individual crystals obtained in accordance with the present invention are shown in FIG. 2, below.

Average diameter measurements of the crystals were determined by laser granulometry.

Laser granulometry is a technique well known in the art. Average particle size can be determined on any particle size analyser known for such purpose, for example a CILAS 1180 No. 516 instrument. Measurements can be made in accordance with the ISO standard 13320-1 (2009 revision) using the Fraunhofer method with water as carrier liquid and an Obscuration Index of 24.

As stated above, the fact that (−)-Ambrox appears in crystal form in a bioconversion medium, as well as the physical characteristics of the crystals, that is, their size and density, is particularly relevant in terms of the efficiency of isolation of (−)-Ambrox and ultimately its clarity and olfactive purity.

More specifically, it was possible to efficiently separate the crystals from the bioconversion medium including particulate material, for example cell debris, as well as any by-products, impurities and the like, by means of a size separation step, that is, a separation step that exploits the physical characteristics of the crystals, such as size, shape and/or density, more specifically a filtration or decantation step.

Furthermore, the efficient separation of crystals from not only particulate and other material, but also from a multi-component and highly coloured bioconversion medium also enables the isolation of (−)-Ambrox from impurities, including any by-products that may be formed, which may include structural (constitutional) isomers and stereo-isomers, such as those stereo- or constitutional-isomers referred to herein below as compounds (II), (III) and (IV), which unlike (−)-Ambrox do not crystallize in the bioconversion medium. Thus, as a result of the manner in which (−)-Ambrox crystallizes, as well as the size separation step enables the applicant to obtain (−)-Ambrox as an essentially colourless and olfactively pure product.

Accordingly, the invention provides in another of its aspects a method of preparing a solid form of (−)-Ambrox, said method comprising the steps of:—

I) forming crystalline (−)-Ambrox in a bioconversion medium by means of a biocatalytic process; and II) separating the crystalline (−)-Ambrox from the bioconversion medium.

The bioconversion medium, from which the crystalline (−)-Ambrox can be separated by means of the present invention, may contain all manner of impurities, such as particulate material, by-products, and the like. In particular, when the bioconversion is carried out using a microbial biocatalyst, the crystalline (−)-Ambrox can be separated from a bioconversion medium containing cells and cell debris.

In a particular embodiment of the invention, the separation step is a size separation step that allows separation of not only the crystalline material from the liquid phase or phases, but also permits separation of the crystals from any particulate material, such as cells or cell debris, owing to the physical characteristics of the crystals, such as their size, shape and/or density.

In a more particular embodiment, the size separation step is a filtration step, a decantation step, or a combination of filtration and decantation.

Alternatively or in addition to filtration and/or decantation, the (−)-Ambrox may also be pelletized. Preferably, the crystals of (−)-Ambrox are melted prior to filtration and/or decantation and/or palletization.

In a particular embodiment of the invention, prior to the separation step ii) the bioconversion medium can be heated in order to melt the crystals of (−)-Ambrox, before gradual cooling to allow the (−)-Ambrox to recrystallize. For this purpose, the bioconversion medium may be heated to a temperature of at least 55° C. Heating may carried out gradually over a period ranging from about 15 minutes up to about 2 hours, before cooling slowly to a temperature of about 20° C. or lower, e.g. to 4° C., at a rate of a few degrees per hour, more particularly about 5° C. per hour. After this cooling, the bioconversion medium may be maintained at 4° C. during 8 hours.

The recrystallization step enables larger and more uniform crystals to form, which helps to further improve the efficiency of the separation step.

It was surprisingly found that the addition of a salt to the bioconversion medium prior to recrystallization aided crystal growth, which further increased the size of the crystals, and created a more uniform distribution of crystal size. Particular salts include inorganic salts, and in particular calcium chloride, sodium chloride, magnesium chloride, potassium chloride and lithium chloride.

The increased size and improved uniformity of the crystals can facilitate the subsequent size separation step as smaller or broken crystals that were formed during the bioconversion process are eliminated.

The size separation step can be carried out by filtration, employing a filter that has a mesh size that is large enough to allow particulate material contained in the bioconversion medium, for example cells and cell debris, to pass through the filter with the filtrate, whilst being small enough to capture the all, or substantially all, of the (−)-Ambrox crystals as the retentate.

The crystals of (−)-Ambrox can be filtered over a suitable filter bed having a mesh size that is between 10 to 100 microns or larger, preferably greater than about 50 microns, 60 microns, 70 microns, 80 microns, 90 microns, or 100 microns.

Regarding the means by which filtration is performed, any of the known filtration techniques and equipment can be employed. However, preference is afforded to techniques that are industrially scalable. Centrifugal filtration is particularly suitable in this regard.

Filter centrifuge apparatus are widely known in the art (see for example, Chapter 1 of "Separation and Purification Techniques in Biotechnology" by Frederick J. Dechow Noves; Publications ISBN No. 0-8155-1197-3. The apparatus may be any variant thereof including a separation plate centrifuge, or a cylinder type centrifuge.

It is possible to conduct the filtration step on a continuous screen centrifuge, such as a Siebtechnic H250 apparatus. Mesh size can be any size referred to hereinabove, and in particular about 100 microns or greater. Having regard to the efficiency of the filtration process, the centrifuge may be operated between 500 and 2500 g, and more particularly about 2000 g, still more particularly 2028 g. The rate at which the bioconversion medium is fed into the centrifuge can be optimized to provide the most efficient filtration possible, and may include a rate of 300 to 800 kg/hour, and more particularly about 400 kg/hour, more particularly still about 430 kg/hour.

Alternatively, the size separation step may be carried out by means of a decantation step.

In a process of decantation, the bioconversion medium is fed into suitable decantation apparatus and is therein subjected to gravitation acceleration. In accordance with Stoke's Law, smaller and less dense particulate material in the bioconversion medium, for example cells or cell debris, are retained suspended in a supernatant containing other impurities of the bioconversion process, whereas the relatively large and dense crystals of (−)-Ambrox settle as a sediment on a bed provided therefor. The separation can be carried out statically, or it can be facilitated by subjecting the bioconversion medium to a force of up to 6000 g, more particularly about 500 to 1500 g, and more particularly about 1000 g, and more particularly still 1170 g.

The supernatant may be drawn off and discarded, or alternatively subjected to further decantation steps to separate and recover any crystalline (−)-Ambrox that remained in the supernatant.

Decantation apparatus are generally known in the art. A particular apparatus that is suitable for use in the present invention is a Guinard Decanter, for example a model D1LC20HC. The bioconversion medium may be fed into the apparatus at any desirable rate optimized to provide an efficient throughput, for example up to 500 kg/hour and more particularly about 300 to 400 kg/hour.

Filtration and decantation may be employed individually as steps in the particle size separation process, or a combination of filtration and decantation steps may be used. Crystals of (−)-Ambrox separated from the reaction medium in accordance with the size separation step may be washed to remove any residual particulate material, for example cells or cell debris, as well as any other residual impurities, such as by-products, solvents, unreacted substrate and the like.

Solvents useful to wash the crystals include any solvents in which (−)-Ambrox is insoluble or very sparingly soluble at the temperature at which the washing step is carried out. More particularly, (−)-Ambrox is deemed insoluble or very sparingly soluble in solvents in which the solubility of (−)-Ambrox is 10 wt % or less, at 5° C.

Washing may be carried out using water, water-miscible solvents or mixtures thereof. Suitable water-miscible solvents include lower alkanols, such as ethanol.

More particularly, the crystals are washed with water, for example 3 masses of water to 1 mass of crystals. Multiple washings may be carried out.

After washing, the filtrate, or the supernatant as the case may be, can be discarded.

Recovery of the (−)-Ambrox can be achieved by its mechanical removal from the filter or decanter apparatus or belt filter (e.g. modifications 7, 8, 9 and 20), collected and dried. The (−)-Ambrox can be used in this form, without further purification or polishing, in perfumery applications.

However, more typically, the (−)-Ambrox can be dissolved in a solvent and subjected to further purification steps as set forth in more detail below, before being employed in perfumery application.

The (−)-Ambrox obtained from the separation step can be dissolved in a suitable solvent. Suitable solvents include toluene, or lower alkanols, such as ethanol, e.g. 96% ethanol.

The solution of (−)-Ambrox may be subjected to a filtration step on a filter having a mesh size suitable to remove and separate any residual particulate material, such as cells or cell debris from the (−)-Ambrox that might not have been removed during the particle size separation step, and subsequent washing. A suitable mesh size might be starting from between 0.22 to 1 microns and up to 150 microns. Any filtration techniques and apparatus known in the art to be suitable for such a purpose may be employed in accordance with the invention.

Ethanol can be used to dissolve the crystals. The quantity of ethanol used is preferably that sufficient to dissolve the (−)-Ambrox at about 25° C., typically about 1 part crystal to 4 parts ethanol and the solution filtered over a 0.22 micron filter (e.g. KDS 15) at 1 bar pressure and ambient temperature. In addition, it may finally be filtered over a 0.22 micron filter as a polishing filtration step.

Filtration at this stage to remove any remaining particulate material, such as cells or cell debris, can have a deodorizing effect on (−)-Ambrox. This is because residual cells or cell debris can be the cause of very unpleasant off-notes if it remains in the finished (−)-Ambrox product. The off-note can be particularly lingering owing to the fixative properties of (−)-Ambrox, and so its removal is particularly important for purposes of obtaining olfactively pure (−)-Ambrox.

The (−)-Ambrox can be subjected to an optional bleaching step to remove any residual colouration that might be present despite the efficient separation of the crystals from the bioconversion medium. For fragrance applications, even lightly coloured (−)-Ambrox is not desirable as a raw material and so it is particularly important to clarify (−)-Ambrox to the greatest extent possible if the product is to be valued for fragrance applications, and particularly fine fragrance applications, or perfumed cosmetic applications.

For this purpose, a solution of the solubilised (−)-Ambrox crystals can be contacted with a bleaching agent, such as activated montmorillonite clays and/or activated charcoal. Suitable bleaching agents include TONSIL FF, more particularly TONSIL 412FF, and/or animal black or Norit.

Optionally, as an alternative to adding a bleaching agent to a solution of (−)-Ambrox, the solution can be concentrated and the solid residue distilled under reduced pressure.

The bleaching agent may be added to a refluxing solution (80 to 85° C.) of (−)-Ambrox. For this purpose, the bleaching agent may be added as a suspension in a suitable solvent, such as ethanol. Contact of the bleaching agent and the solution may be for a period of time in the order of 30 minutes. Thereafter, the bleaching agent is removed by filtration, for example, using a 25 micron filter.

Bleaching agents might not be effective in reducing the colour of highly coloured reaction mixtures, and certainly not to the extent required or suitable for perfumery applications. However, owing to the efficient isolation and purification of (−)-Ambrox from the bioconversion medium described herein, the solution of (−)-Ambrox is already substantially colourless, and obtaining the desired bleaching effect for this solution is rather less difficult. As a result, it is possible to obtain a form of (−)-Ambrox, notwithstanding that it is a product of a biocatalytic process, which possesses a desirable lightness and hue that is expected if the product is to be employed in perfumery applications.

In accordance with the method of the present invention, the deodourized and decolourized (−)-Ambrox solution may be provided in a solid form by removal of the solvent. Solvent removal can be effected by re-crystallisation or by evaporation. The recovered (−)-Ambrox may be obtained in its re-crystallized form or as a solid residue, which may be comminuted, depending on the manner in which the solvent removal is carried out.

Solvent may be removed by evaporation and the residual solid may be recovered, for example by comminution, stored and used in perfumery applications.

Alternatively, the residual solid may dissolved in a suitable recrystallizing solvent. A suitable solvent for the purpose is a water-miscible alkanol, such as ethanol, or mixtures of said alkanol with water. The recrystallization solvent can be heated to about 75-80° C. for 15 minutes, before gradual cooling to about 10-15° C. The resultant crystals can be recovered by filtration and dried, optionally under vacuum (e.g. 0.5 bar).

As a result of the method according to the present invention, (−)-Ambrox can be obtained in solid form that is substantially colourless and is olfactively pure.

Accordingly, the invention provide in another of its aspects, a substantially colourless solid form of (−)-Ambrox, which solid form of (−)-Ambrox has an $L^*$ value of 90 or more; an $a^*$ value of less than 1 and greater the −1; and a $b^*$ value, which is less than 8, wherein $L^*$, $a^*$ and $b^*$ values represent the CIELAB system's chromaticity coordinates.

The solid form of (−)-Ambrox according to the invention exhibits a high degree of lightness or brightness and a low degree of yellowness. This is important for perfumery applications, and particularly for fine fragrance or perfumery intended for use in cosmetics, as the visual aesthetic as well as odour are highly valued, and a perfumed product should not be discoloured as a result of the incorporation of a perfumery ingredient.

(−)-Ambrox according to the invention has an $L^*$ value indicating the lightness of 90 or more and a $b^*$ value indicating the blue-yellow hue of 8 or less. The $L^*$ value is preferably 92 or more, or even 93 or more. The $b^*$ value is preferably 5 or less, or even 4 or less.

The $L^*$ value is a value specifying the lightness of a substance and is indicated by a value between 0 and 100. An $L^*$ value of 100 indicates the brightest state (completely white), and an $L^*$ value of 0 indicates the darkest state (completely black).

The $b^*$ value specifies the blue-yellow hue of a substance. The larger is the $b^*$ value, the higher is the degree of yellowness. The smaller is the $b^*$ value, the higher is the degree of blueness.

The $L^*$ value and the $b^*$ value may be indicated by Lab chromaticity coordinates according to a color difference indication method. The $L^*$ value and the $b^*$ value may be measured using any suitable commercially available spectrophotometer, such as the Minolta CM3500d.

The spectrophotometer should be powered up for at least one hour before making a measurement. A glass container provided therefor should be half filled with the solid product to be measured taking care to ensure that the bottom of the container is fully covered by the product. Thereafter, the filled container should be placed in the sample stand provided therefor. The sample key on the instrument should be pressed and the $L^*$ $a^*$ $b^*$ values read off the display panel.

Before taking any readings, the instrument should be calibrated for the zero and 100% reflection by placing black and white objects provided therefor on the window of the instruments optical sensor.

In an embodiment of the invention the solid form of (−)-Ambrox is the crystalline form characterized above.

In an embodiment of the invention, the solid form of (−)-Ambrox is a bioconversion product.

In an embodiment of the invention the solid form of (−)-Ambrox is a bioconversion product formed according to a bioconversion process as described herein.

In still another aspect of the invention there is provided a form of (−)-Ambrox obtained by a biocatalytic process as herein described.

In a more particular embodiment the biocatalytic process is a microbial biocatalytic process.

In still another aspect of the invention there is provided the use of a form of (−)-Ambrox herein defined, in fragrance or flavour applications.

The principles, uses and implementations of the present invention may be further illustrated and understood with reference to the accompanying detailed description and Figures. Before explaining a particular embodiment of the invention in more detail, however, it is to be understood that the invention is not limited in its principles to the details described hereunder.

DETAILED DESCRIPTION OF THE INVENTION

In accordance with the present invention, a crystalline form of (−)-Ambrox is obtained by a bioconversion process. The precise nature of the bioconversion (for example, the nature of the biocatalyst used, the substrate, the reaction conditions for the bioconversion of the substrate, and the like) is not critical provided the conditions are such as to allow the bio-catalyst to convert the substrate to produce (−)-Ambrox in a form that crystallizes in the bioconversion medium.

In an embodiment of the present invention, a substrate consisting of a mixture of 7E,3E/Z-homofarnesol undergoes a bioconversion process, whereby the homofarnesol mixture is enzymatically cyclized in the presence of a recombinant microorganism expressing an enzyme, in particular a Squalene Hopene Cyclase (SHC) biocatalyst capable of bioconverting homofarnesol to (−)-Ambrox, to yield a reaction mixture from which (−)-Ambrox can be isolated in a substantially colourless and olfactively pure form with surprisingly efficient downstream processing.

In one aspect of the invention there is provided the enzyme-catalyzed cyclisation of homofarnesol to provide a reaction mixture comprising (−)-Ambrox, wherein the homofarnesol comprises a mixture of 7E,3E/Z-geometric isomers of homofarnesol, and wherein the reaction is carried out in the presence of a recombinant microorganism producing the enzyme, more particularly a substantially whole or intact recombinant microorganism producing the enzyme.

The cyclization reaction is carried out in the presence of an SHC biocatalyst capable of bioconverting homofarnesol to (−)-Ambrox.

The SHC biocatalyst is a wild-type or a variant enzyme or is a microorganism expressing a gene encoding the SHC enzyme, preferably a recombinant *E. coli* microorganism. The SHC biocatalyst can be used in any form such as but not limited to a purified SHC enzyme, a crude extract containing an SHC enzyme or an immobilised SHC enzyme (e.g. on a carrier), or the biocatalyst can be a microorganism having produced or producing the SHC enzyme, such as an intact recombinant whole cell and/or fragmented cell or a membrane fraction containing the SHC enzyme.

In a particular embodiment of the present invention, the homofarnesol mixture is enriched in the 7E,3E-geometric isomer.

In a more particular embodiment, the homofarnesol mixture is at least 55/45 by weight 7E,3E/7E,3Z.

In a more particular embodiment, the homofarnesol mixture is at least 70/30 by weight 7E,3E/7E,3Z.

In a still more particular embodiment, the homofarnesol mixture is at least 80/20 by weight 7E,3E/7E,3Z In a still more particular embodiment, the homofarnesol mixture is at least 90/10 by weight 7E,3E/7E,3Z.

In a still more particular embodiment, the homofarnesol mixture is at least 95/5 by weight 7E,3E/7E,3Z.

In a particular embodiment of the present invention, the homofarnesol mixture consists of 7E,3E/Z-geometric isomers and no other geometric isomers of homofarnesol.

The skilled person understands that the term 7E, 7Z, 3E or 3Z used in connection with homofarnesol refers respectively to the orientation of the double bond at the 7-position and 3-position of homofarnesol. The 7E,3E-homofarnesol compound has the CAS No. 459-89-2, whereas the 7E,3Z-homofarnesol compound has the CAS No. 138152-06-4. The use of the term 7E, 3E/Z-homofarnesol refers to a mixture of the compounds.

Methods of obtaining homofarnesol mixtures useful as a substrate in the cyclisation reaction in accordance with the method of the present invention are set forth in the co-pending applications PCT/EP2014/072891 (published as WO 2015/059293) and PCT/EP2014/072882 (published as WO 2015/059290) referred to above, which are hereby incorporated by reference in their entirety. In general terms, they describe a synthesis of homofarnesol mixtures that proceeds by converting farnesene, more particularly alpha-farnesene and/or beta-farnesene, to its corresponding cyclopropanated farnesene derivative, using an organic solution of an N-alkyl-N-nitroso urea. The cyclopropanated derivative then undergoes ring-opening and rearrangement reactions in the presence of a Bronsted acid to afford the homofarnesol mixture, which is selective for the 7E,3E geometric isomer. Using farnesene, as a starting material is particularly preferred because it ensures that the E-configuration of the double bond at the 7 position of homofarnesol is fixed.

Specific reaction conditions, which form particular embodiments of the present invention, are set forth in the co-pending applications, as well as the examples hereinbelow, and do not require more elaboration here.

The cyclization of homofarnesol to provide a reaction mixture containing (−)-Ambrox may be catalysed by Squalene Hopene Cyclase (SHC). SHC may be a wild type enzyme (e.g. SEQ ID No. 1), or a variant thereof (e.g. SEQ ID No. 2, or SEQ ID No. 4). SHC can be obtained from *Alicyclobacillus acidocaldarius* (*Bacillus acidocaldarius*), *Zymomonas mobilis* or *Bradyrhizobium japonicum* (as set forth in Example 3b of US 2012/0135477 A1).

However, the enzyme can also be produced by recombinant means, using techniques that are generally known in the art.

The term "recombinant" as used with respect to the production of enzymes shall refer to enzymes produced by recombinant DNA techniques, i.e., produced from cells transformed by an exogenous DNA construct encoding the desired enzyme. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

Nucleic acid molecule(s) is/are operatively linked to expression control sequences allowing expression in prokaryotic and/or eukaryotic host cells. As used herein, "operatively linked" means incorporated into a genetic construct so that expression control sequences effectively control expression of a coding sequence of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include, but are not limited to, regulatory elements directing constitutive expression or which allow inducible expression like, for example, CUP-1 promoter, the tet-repressor as employed, for example, in the tet-on or tet-off systems, the lac system, the trp system regulatory elements. By way of example, Isopropyl β-D-1-thiogalactopyranoside (IPTG) is an effective inducer of protein expression in the concentration range of 100 µM to 1.0 mM. This compound is a molecular mimic of allolactose, a lactose metabolite that triggers transcription of the lac operon, and it is therefore used to induce protein expression where the gene is under the control of the lac operator.

Similarly, nucleic acid molecule(s) can form part of a hybrid gene encoding additional polypeptide sequences, for example, a sequence that functions as a marker or reporter. Examples of marker and reporter genes including beta-lactamase, chloramphenicol acetyl-transferase (CAT), adenosine deaminase (ADA), aminoglycoside phosphotransferase di-hydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

Recombinant polynucleotides can encode SHC enzymes such as the wild type SHC or a variant thereof, which may be inserted into a vector for expression and optional purification. One type of vector is a plasmid representing a circular double stranded DNA loop into which additional DNA segments are ligated. Certain vectors can control the expression of genes to which they are functionally linked. These vectors are called "expression vectors". Usually, expression vectors suitable for DNA recombination techniques are of the plasmid type. Typically, an expression vector comprises a gene such as the wild type SHC or a variant thereof. In the present description, the terms "plasmid" and "vector" are used inter-changeably since the plasmid is the vector type most often used.

Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host is augmented through the stable introduction of one or more recombinant genes. However, autonomous or replicative plasmids or vectors can also be used within the scope of this disclosure. Moreover, the present disclosure can be practiced using a low copy number, e.g., a single copy, or high copy number plasmid or vector.

In a preferred embodiment the vector of the present disclosure comprises plasmids, phagemids, phages, cosmids, artificial bacterial and artificial yeast chromosomes, knock-out or knock-in constructs, Synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are produced within the cell upon introduction of the vector. The diverse gene substrates may be incorporated into plasmids. The plasmids are often standard cloning vectors, e.g., bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more of the following nucleotide sequences as is well known in the art. For in vivo recombination, the gene to be recombined with the genome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transformed cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which can be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which can be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp, yeast host cells, such as *S. cerevisiae*, insect host cells, such as *Spodoptora frugiperda* or human host cells, such as HeLa and Jurkat.

Specifically, the cell is a eukaryotic cell, preferably a fungal, mammalian or plant cell, or prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eukaryotic cell lines. Suitable bacterial cells include without limitation *E. coli*.

Preferably prokaryotes, such as *E. coli, Bacillus, Streptomyces*, or mammalian cells, like HeLa cells or Jurkat cells, or plant cells, like *Arabidopsis*, may be used.

Preferably the cell is an *Aspergillus* sp or a fungal cell, preferably, it can be selected from the group consisting of the genera *Saccharomyces, Candida, Kluyveromyces, Hansenula, Schizosaccharomyces, Yarrowia, Pichia* and *Aspergillus*.

Preferably the *E. coli* host cell is an *E. coli* host cell which is recognized by the industry and regulatory authorities (including but not limited to an *E. coli* K12 host cell or as demonstrated in the Examples, an *E. coli* BL21 host cell).

One preferred host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

In one embodiment, the recombinant *E. coli* microorganism comprises nucleotide sequences encoding SHC genes or functional equivalents/homologies thereof including but not limited to variants, homologues mutants, derivatives or fragments thereof.

Another preferred host cell to use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells is performed, in a conventional manner. The culture medium contains a carbon source, at least one nitrogen source and inorganic salts, and vitamins are added to it. The constituents of this medium can be the ones which are conventionally used for culturing the species of microorganism in question.

Carbon sources of use in the instant method include any molecule that can be metabolized by the recombinant host cell to facilitate growth and/or production of (−)-Ambrox. Examples of suitable carbon sources include, but are not limited to, sucrose (e.g., as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

The suitability of a recombinant host cell microorganism for use in the methods of the present disclosure may be determined by simple test procedures using well known methods. For example, the microorganism to be tested may be propagated in a rich medium (e.g., LB-medium, Bacto-tryptone yeast extract medium, nutrient medium and the like) at a pH, temperature and under aeration conditions commonly used for propagation of the microorganism. Once recombinant microorganisms (i.e. recombinant host cells) are selected that produce the desired products of bioconversion, the products are typically produced by a production host cell line on the large scale by suitable expression systems and fermentations, e.g. by microbial production in cell culture.

In one embodiment of the present disclosure, a defined minimal medium such as M9A is used for cell cultivation. The components of M9A medium comprise: 14 g/L $KH_2PO_4$, 16 g/L $K_2HPO_4$, 1 g/L $Na_3Citrate.2H_2O$, 7.5 g/L $(NH_4)_2SO_4$, 0.25 g/L $MgSO_4.7H_2O$, 0.015 g/L $CaCl_2.2H_2O$, 5 g/L of glucose and 1.25 g/L yeast extract).

In another embodiment of the present disclosure, nutrient rich medium such as LB (Luria-Bertani) was used. The components of LB comprise: 10 g/L tryptone, 5 g/L yeast extract, 5 g/L NaCl).

Other examples of Mineral Medium and M9 Mineral Medium are disclosed, for example, in U.S. Pat. No. 6,524, 831 B2 and US 2003/0092143 A1.

The recombinant microorganism may be grown in a batch, fed batch or continuous process or combinations thereof. Typically, the recombinant microorganism is grown in a fermentor at a defined temperature in the presence of a suitable nutrient source, e.g., a carbon source, for a desired period of time to bioconvert homofarnesol to (−)-Ambrox in a desired amount.

The recombinant host cells may be cultivated in any suitable manner, for example by batch cultivation or fed-batch cultivation. As used herein, the term "batch cultivation" is a cultivation method in which culture medium is neither added nor withdrawn during the cultivation. As used herein, the term "fed-batch" means a cultivation method in which culture medium is added during the cultivation but no culture medium is withdrawn.

One embodiment of the present disclosure provides a method of producing (−)-Ambrox in a cellular system comprising producing wild type SHC or variants thereof under suitable conditions in a cellular system, feeding homofarnesol to the cellular system, converting the homofarnesol to (−)-Ambrox using the SHC or variants produced using the cellular system, collecting (−)-Ambrox from cellular system and isolating the (−)-Ambrox from the system. Expression of other nucleotide sequences may serve to enhance the method. The bioconversion method can include the additional expression of other nucleotide sequences in the cellular system. The expression of other nucleotide sequences may enhance the bioconversion pathway for making (−)-Ambrox.

A further embodiment of the present disclosure is a bioconversion method of making (−)-Ambrox comprising growing host cells comprising wild type SHC or variant genes, producing wild type SHC or variant enzymes in the host cells, feeding homofarnesol (e.g. EEH) to the host cells, incubating the host cells under conditions of pH, temperature and solubilizing agent suitable to promote the conversion of homofarnesol to Ambrox and collecting (−)-Ambrox. The production of the wild type SHC or variant enzymes in the host cells provides a method of making (−)-Ambrox when homofarnesol is added to the host cells under suitable reaction conditions. Achieved conversion may be enhanced by adding more biocatalyst and SDS to the reaction mixture.

The recombinant host cell microorganism may be cultured in a number of ways in order to provide cells in suitable amounts expressing the wild type SHC or variant enzymes for the subsequent bioconversion step. Since the microorganisms applicable for the bioconversion step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent bioconversion step of the present disclosure. Typically, the cells are grown to a particular density (measurably as optical density (OD)) to produce a sufficient biomass for the bioconversion reaction. The cultivation conditions chosen influence not only the amount of cells obtained (the biomass) but the quality of the cultivation conditions also influences how the biomass becomes a biocatalyst. The recombinant host cell microorganism expressing the wild type SHC or variant genes and producing the wild type SHC or variant enzymes is termed a biocatalyst which is suitable for use in a bioconversion reaction. In some embodiments the biocatalyst is a recombinant whole cell producing wild type SHC or variant enzymes or it may be in suspension or an immobilized format.

In one embodiment, the biocatalyst is produced in sufficient amounts (to create a sufficient biomass), harvested and washed (and optionally stored (e.g. frozen or lyophilized)) before the bioconversion step.

In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process while reducing costs. The culture medium used to grow the cells is also suitable for use in the bioconversion reaction provided that the reaction conditions are adjusted to facilitate the bioconversion reaction.

The bioconversion methods of the present disclosure are carried out under conditions of time, temperature, pH and solubilizing agent to provide for conversion of the homofarnesol feedstock to (−)-Ambrox. The pH of the reaction mixture may be in the range of 4-8, preferably, 5 to 6.5, more preferably 4.8-6.0 for the SHC variant enzymes and in the range of from about pH 5.0 to about pH 7.0 for the wild type SHC enzyme and can be maintained by the addition of buffers to the reaction mixture. An exemplary buffer for this purpose is a citric acid buffer. Alternatively, tap water or deionized water supplemented with or without NaCl at 0.5% or 0.9% can be used as a buffer substitute when adjusted to a pH, which provides optimal biocatalyst activity, including but not limited to the pH range of 5.0 to 8.0.

Accordingly, the invention provides in another aspect a solid form of (−)-Ambrox formed or obtainable by a bioconversion process disclosed herein, wherein the bioconversion reaction is carried out in a medium using tap water or de-ionised water as a buffer substitute and in the pH range which ensures optimal biocatalytic activity, preferably a pH range 5.0-8.0.

The preferred temperature is between from about 15° C. and about 45° C., preferably about 20° C. and about 40° C. although it can be higher, up to 55° C. for thermophilic organisms especially if the wild type enzyme from a thermophilic microorganism is used. The temperature can be kept constant or can be altered during the bioconversion process.

It may be useful to include a solubilizing agent (e.g. a surfactant, detergent, solubility enhancer, water miscible organic solvent and the like) in the bioconversion reaction. Examples of surfactants include but are not limited to Triton X-100, Tween 80, taurodeoxycholate, Sodium taurodeoxycholate, Sodium dodecyl sulfate (SDS), and/or sodium lauryl sulfate (SLS).

The Applicant has selected and identified SDS as a particularly useful solubilizing agent from a long list of other less useful solubilizing agents. In particular, the Applicant identified SDS as a remarkably better solubilizing agent than e.g. Triton X-100 in terms of reaction velocity and yield for the homofarnesol to (−)-Ambrox bioconversion reaction.

Without wishing to be bound by theory, the use of SDS with recombinant microbial host cells may be advantageous as the SDS may interact advantageously with the host cell membrane in order to make the SHC enzyme (which is a membrane bound enzyme) more accessible to the homofarnesol substrate. In addition, the inclusion of SDS at a suitable level in the reaction mixture may improve the properties of the emulsion (homofarnesol in water) and/or improve the access of the homofarnesol substrate to the SHC enzyme within the host cell while at the same time preventing the disruption (e.g. denaturation/inactivation of the wild type SHC or variant enzyme).

The concentration of the solubilising agent (e.g. SDS) used in the bioconversion reaction is influenced by the biomass amount and the substrate (EEH) concentration. That is, there is a degree of interdependency between the solubilising agent (e.g. SDS) concentration, the biomass amount and the substrate (EEH) concentration. By way of example, as the concentration of homofarnesol substrate increases, sufficient amounts of biocatalyst and solubilising agent (e.g. SDS) are required for an efficient bioconversion reaction to take place. If, for example, the solubilising agent (e.g. SDS) concentration is too low, a suboptimal homofarnesol conversion may be observed. On the other hand, if, for example, the solubilising agent (e.g. SDS) concentration is too high, then there may be a risk that the biocatalyst is affected through either the disruption of the intact microbial cell and/or a denaturation/inactivation of the SHC/HAC enzyme.

The selection of a suitable concentration of SDS in the context of the biomass amount and substrate (EEH) concentration is within the knowledge of the Skilled Person. By way of example, a predictive model is available to the Skilled Person to determine the suitable SDS, substrate (EEH) and biomass concentrations.

The temperature of the bioconversion reaction for a wild type SHC enzyme is from about 45-60° C., preferably 55° C.

The pH range of the bioconversion reaction for a wild type SHC enzyme is from about 5.0 to 7.0, more preferably from about 5.6 to about 6.2, even more preferably about 6.0. The temperature of the bioconversion reaction for a SHC variant enzyme is about 34° C. to about 50° C., preferably about 35° C.

The pH of the bioconversion reaction for a SHC variant enzyme is about 4.8-6.4, preferably about 5.2-6.0.

Preferably the solubilising agent used in the bioconversion reaction is SDS.

The [SDS]/[cells] ratio is in the range of about, 10:1-20:1, preferably about 15:1-18:1, preferably about 16:1 when the ratio of biocatalyst to EEH homofarnesol is about 2:1.

The SDS concentration in the bioconversion reaction for a SHC variant enzyme is in the range of about 1-2%, preferably in the range of about 1.4-1.7%, even more preferably about 1.5% when the homofarnesol concentration is about 125 g/l EEH and the biocatalyst concentration is 250 g/l (corresponding to an OD of about 175 (650 nm)).

The ratio of biocatalyst to EEH homofarnesol substrate is in the range of about 0.5:1-2:1, in some embodiments 2:1, preferably about 1:1 or 0.5:1.

In some embodiments, (−)-Ambrox is produced using a biocatalyst to which the homofarnesol substrate is added. It is possible to add the substrate by feeding using known means (e.g. peristaltic pump, infusion syringe and the like). Homofarnesol is an oil soluble compound and is provided in an oil format. Given that the biocatalyst is present in an aqueous phase, the bioconversion reaction may be regarded as a two phase system when homofarnesol is added to the bioconversion reaction mixture. This is the case even when a solubilizing agent (e.g. SDS) is present.

Further details of suitable bioconversion process conditions are disclosed in the examples, set forth herein below.

The bioconversion process produces a bioconversion medium containing the desired (−)-Ambrox, and also a number of by-products. More particularly, the medium contains, in addition to (−)-Ambrox a complex mixture of by-products, including a novel constitutional isomer of (−)-Ambrox according to the formula (II), as well as known stereo isomers of (−)-Ambrox according to the formulae (III) and (IV)

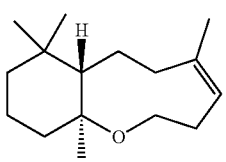

(II)

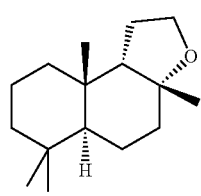

(III)

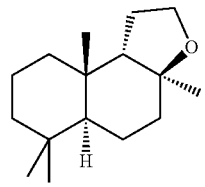

(IV)

The applicant believes, although does not intend to be bound by any particular theory, that the compound of formula (II) is formed by the cyclization of the 7E,3Z-geometric isomer of homofarnesol. It has been described as practically odourless, with a detection threshold of >500 ng/l.

As stated above, the applicant believes that the compound of formula (II) is a novel molecule, and as such, this compound forms a further aspect of the present invention.

Perfume ingredients and perfume compositions consisting of or comprising the compound (II), as well as perfumed articles containing same, form additional aspects of the invention.

The use of the compound of formula (II) as a perfume ingredient in perfumery applications, such as fine perfumes or functional perfume compositions such as personal care, household care and fabric care compositions, forms further additional aspects of the invention.

Mixtures of (−)-Ambrox and an olfactory acceptable amount of compound (II) forms still another aspect of the present invention.

The term "olfactory acceptable amount" as used herein in relation to the compound of formula (II), or any of the other by-products (III) or (IV), or indeed, any material that may be present as an impurity in (−)-Ambrox formed in accordance with a method of the present invention, is understood to mean that the compound or material is present in a mixture with (−)-Ambrox in an amount below its odour detection threshold, or in an amount at which it will not contribute its olfactory characteristics in a way that will affect the olfactory character of (−)-Ambrox. (−)-Ambrox containing an olfactory acceptable amount of any such compound or material would be identifiable to a skilled perfumer as possessing the odour character of commercial grades of (−)-Ambrox, such as AMBROFIX™ obtained by a synthetic procedure ex-sclareol, and available from Givaudan.

In preferred embodiments of the present invention, the reaction mixture contains no, or substantially no, unreacted homofarnesol.

The applicant discovered that homofarnesol was a powerful solvent for (−)-Ambrox as well as for the aforementioned by-products of the bioconversion process. As such, in the presence of appreciable amounts of homofarnesol, (−)-Ambrox and the by-products remain dissolved together in a crude, intractable mixture, from which it is difficult, protracted and costly to separate and ultimately isolate (−)-Ambrox in olfactively pure form. Reducing the level of unreacted homofarnesol in admixture with (−)-Ambrox and the compounds (II), (III) and (IV) was found to considerably facilitate downstream processing and isolation/purify-cation of (−)-Ambrox.

Downstream processing, as will be appreciated by persons skilled in the art, is a critical operation in the manufacture of useful compounds formed by bioconversion processes. As part of the synthesis of a compound, it can affect the compound's physical properties. In the case of the preparation of perfume ingredients by biotech methods, it is desirable that a target compound can be separated from a reaction mixture in olfactively pure form in order that the desired odour characteristics of the target compound are not distorted by odour contributions of the complex mixture of contaminants and by-products that may be present in the fermentation medium or the biocatalyst.

Accordingly, the invention provides a method of isolating and purifying (−)-Ambrox from a bioconversion medium, comprising one or more of the compounds (II), (III) and (IV).

In yet another aspect of the present invention there is provided a method of improving or enhancing the odour of (−)-Ambrox, comprising the steps of separation and purification of (−)-Ambrox from a bioconversion medium containing one or more of the compounds (II), (III) and (IV).

In an isolated and purified form, (−)-Ambrox either does not contain any of the compounds (II), (III) or (IV), or if it does contain any of said compounds, then each should be present in an olfactory acceptable amount.

The bioconversion medium obtained from the bioconversion process described herein above, generally comprises a solid phase containing a crude (−)-Ambrox and a liquid phase or phases consisting of water and an oily phase that may contain any residual homofarnesol and any other oily or oil-soluble impurities or by-products. One or more of by-products (II), (III) and (IV) may be present in such an oily phase.

The solid phase may be separated from the liquid phase or phases by filtration, such as centrifugal filtration, or decantation. Furthermore, and with regard to separation by filtration, by selecting a filter with an appropriate mesh size, it is also possible to separate the solid form of (−)-Ambrox, from particulate material in the bioconversion medium, for example cellular material and/or debris. Decantation, similar to filtration, exploits the difference in particle size between this particulate matter and the solid form of (−)-Ambrox to allow their separation, the former remaining suspended in a supernatant, which can be discarded, whilst the latter can be isolated as a sediment, to be recovered and optionally subjected to further purification steps.

Once the (−)-Ambrox is separated from the particulate material, for example cellular material and/or debris, as well as the liquid phase or liquid phases, it may be washed, before being subjected to further work-up procedures to isolate (−)-Ambrox from any remaining impurities, such as compounds (II), (III) and (IV).

In a particular embodiment of the present invention, said method of isolating and purifying (−)-Ambrox comprises the step of selectively crystallizing (−)-Ambrox from a mixture that may contain one or more of the compounds (II), (III) or (IV), as well as any other impurities formed in the bioconversion medium.

The phrase "selectively crystallizing" refers to a process step whereby (−)-Ambrox is caused to crystallize from a solvent, whilst by-products, such as the compounds (II), (III) and (IV), or any other impurities remain dissolved in the crystallizing solvent, to such an extent that isolated crystalline material contains only (−)-Ambrox, or if it contains any of the by-products, such as compounds (II), (III) or (IV), or any other impurities, then they are present only in olfactory acceptable amounts.

Selective crystallization can occur when (−)-Ambrox crystallizes from the bioconversion medium, whereas any impurities, such as by-products (II), (III) or (IV) that may be present in the bioconversion medium remain in an oily phase. In such a case, any of the compounds (II), (III) and (IV) present in the bioconversion medium can be separated from crystalline (−)-Ambrox by decantation and/or filtration and washing during the same process steps as (−)-Ambrox is being separated from any particulate material, such as cells and cell debris.

(−)-Ambrox crystallized from the bioconversion medium, can be separated by filtration and/or decantation in the manner described above. Thereafter, the crystals can be dissolved in a suitable solvent, and the solution further processed, also in the manner described above. In particular, the solution can be micro-filtered to remove any residual particulate material, such as cells or cell debris; de-colourized by passing it over a suitable bleaching agent; and/or selectively crystallized from the solvent to separate the crystalline (−)-Ambrox from any residues of by-products, such as the compounds (II), (III) or (IV), or any other residual impurities.

Crystallization may be carried out in a suitable organic solvent. The choice of solvent is based on considerations, such as solubility differences at room temperature and at high temperatures, or in boiling solvent; and for the need of an abundance of crystals recoverable in cool solvent. Usually, a compound to be separated is dissolved in a relatively polar solvent and then a relatively less polar solvent can be added to bring the dissolved compound to its solubility limit, whereupon it will start to crystallize. Also, in an industrial process, issues of cost as well as safety of handling are relevant. Suitable solvents include, but are not limited to methanol, acetone, petroleum ether, hexane, t-butyl methyl ether, THF and ethyl acetate. Preferred solvents include ethyl alcohol. Pairs of solvents may also be employed.

In a particularly preferred embodiment of the present invention, selective crystallization is undertaken by dissolving the mixture containing (−)-Ambrox and one or more of the compounds (II), (III) and (IV) in warm ethanol and allowing (−)-Ambrox to selectively crystallize by slowly adding a non-solvent, such as water, to the cooling ethanolic solution.

Considering the close structural relationship of (−)-Ambrox and the by-product compounds (II), (III) and (IV), which are respectively a constitutional isomer and two stereoisomers of (−)-Ambrox, it was remarkable that (−)-Ambrox could be selectively crystallized from such a mixture, to provide (−)-Ambrox in olfactively pure form and in high yields. The skilled person would reasonably anticipate that one or more of the compounds would crystallize under the same or substantially similar conditions as (−)-Ambrox rendering downstream processing far more complex, time-consuming and expensive than was found to be the case.

The surprisingly facile manner in which (−)-Ambrox could be separated from a mixture containing compound (II), (III) and/or (IV) by crystallization represents a particular advantage of the present invention.

The ease with which (−)-Ambrox could be separated by crystallization could be contrasted with the observation that (−)-Ambrox could not be recovered in such a facile manner and in such high yield from a mixture containing (II), (III) and/or (IV) by other purification techniques, such as by rectification, owing to the very similar boiling points of (−)-Ambrox and the by-products (II), (III) and (IV), or by solvent extraction.

The term "olfactively pure" as it is used in relation to (−)-Ambrox, is intended to mean that (−)-Ambrox is free of compounds (II), (III) or (IV), or any other material found in the reaction mixture, or that if such compounds or materials should be present, they are present in olfactory acceptable amounts, as that term is defined herein.

In an embodiment of the invention (−)-Ambrox in olfactively pure form contains less than 5% by weight of any of the compounds (II), (III) or (IV).

In more particular embodiments, (−)-Ambrox in olfactively pure form contains less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, or less than 0.05% by weight of each of the compounds (II), (III) or (IV).

The quality of separation of (−)-Ambrox from the mixture of the compounds (II), (III) and/or (IV) by selective crystallization may be influenced by the composition of the mixture from which it is separated. More particularly, the quality of the separation of (−)-Ambrox from a mixture of compounds (II), (III) and/or (IV) by crystallization was improved when the weight ratio of (−)-Ambrox to the other compounds (II), (III) and (IV) in the mixture was greater than 70:30, more particularly 80:20, more particularly 90:10, still more particularly 95:5, and more particularly still 97:3.

Furthermore, the quality of the separation of (−)-Ambrox by crystallization may be influenced by the amount of unreacted homofarnesol present in the mixture from which it is separated. More particularly, the quality of separation is improved when the level of unreacted homofarnesol is less than 30% by weight, more particularly less than 20 wt %, more particularly less than 10% by weight, more particularly still less than 5 wt % and still more particularly less than 3% by weight, still more particularly less than 2% by weight, and more particularly still less than 1% by weight, based on the weight of the mixture from which (−)-Ambrox is crystallized.

Preferably, the reagents and reaction conditions employed in the bioconversion process of the present invention are such that the reaction proceeds with 100% conversion of homofarnesol, or substantially so, thus leaving no unreacted homofarnesol in the bioconversion medium. However, if unreacted homofarnesol is present, although economically disadvantageous, it can be separated from (−)-Ambrox and other by-products by distillation, or washing crystals of (−)-Ambrox with a suitable solvent, for example.

Accordingly, in a particular embodiment of the invention, there is provided a method of isolating and purifying (−)-Ambrox from a mixture comprising one or more of the compounds (II), (III) and (IV), which mixture is free, or substantially free, of homofarnesol.

In a more particular embodiment, the isolation and purification of (−)-Ambrox from a mixture comprising one or more of the compounds (II), (III) and (IV), and free or substantially free of homofarnesol, is achieved by the selective crystallization of (−)-Ambrox.

(−)-Ambrox obtained according to a method of the present invention is obtained in olfactively pure form. Olfactively pure (−)-Ambrox forms another aspect of the present invention.

(−)-Ambrox in crystalline form forms yet another aspect of the present invention.

(−)-Ambrox formed in accordance with the method of the present invention may be mixed with one or more additional perfume ingredients to form perfume compositions that find use in perfumery applications, including use in fine perfumery, as well as use in consumer products, such as personal care, fabric care and household care applications.

Accordingly, the invention provides in another of its aspects a perfume composition comprising (−)-Ambrox and at least one other perfume ingredient, wherein said perfume composition contains olfactory acceptable amounts of one or more of the compounds (II), (III) or (IV).

BRIEF DESCRIPTION OF THE DRAWINGS

For a greater understanding of the present invention, reference is made to the accompanying Figures, in which:—

Figure 1:
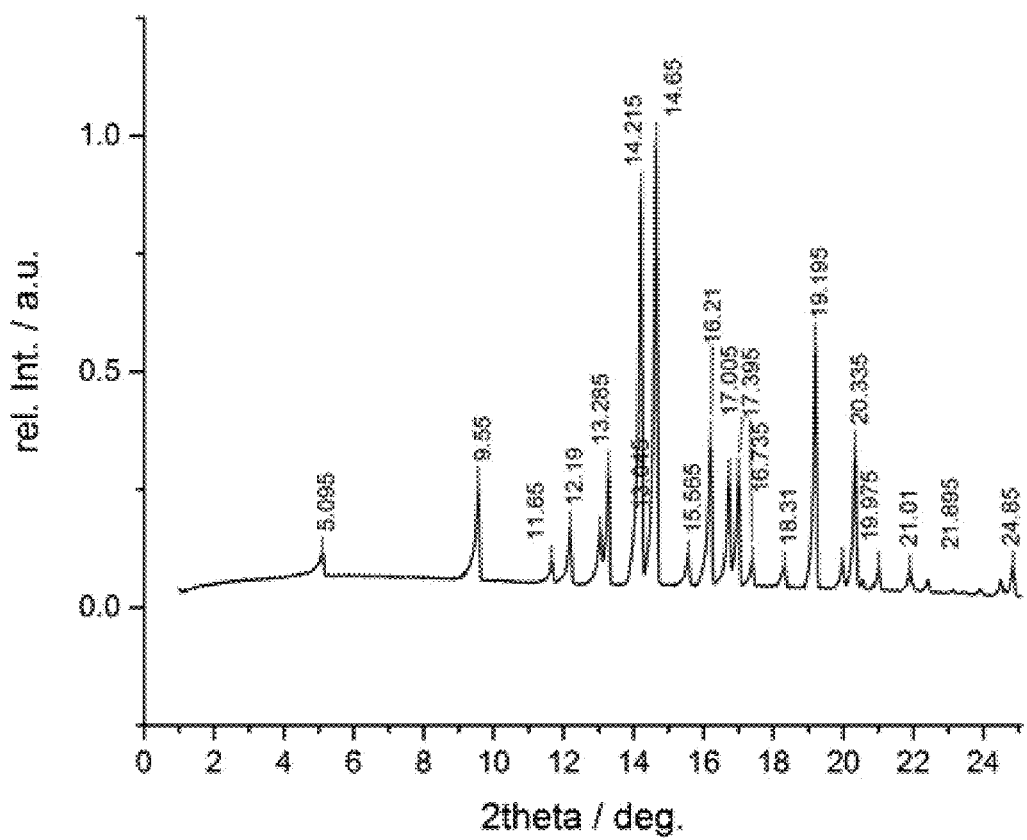
FIG. 1 shows an x-ray diffraction pattern in which the scale of the abscissa is degrees 2-theta, and the ordinate is the intensity in counts
Figure 2:
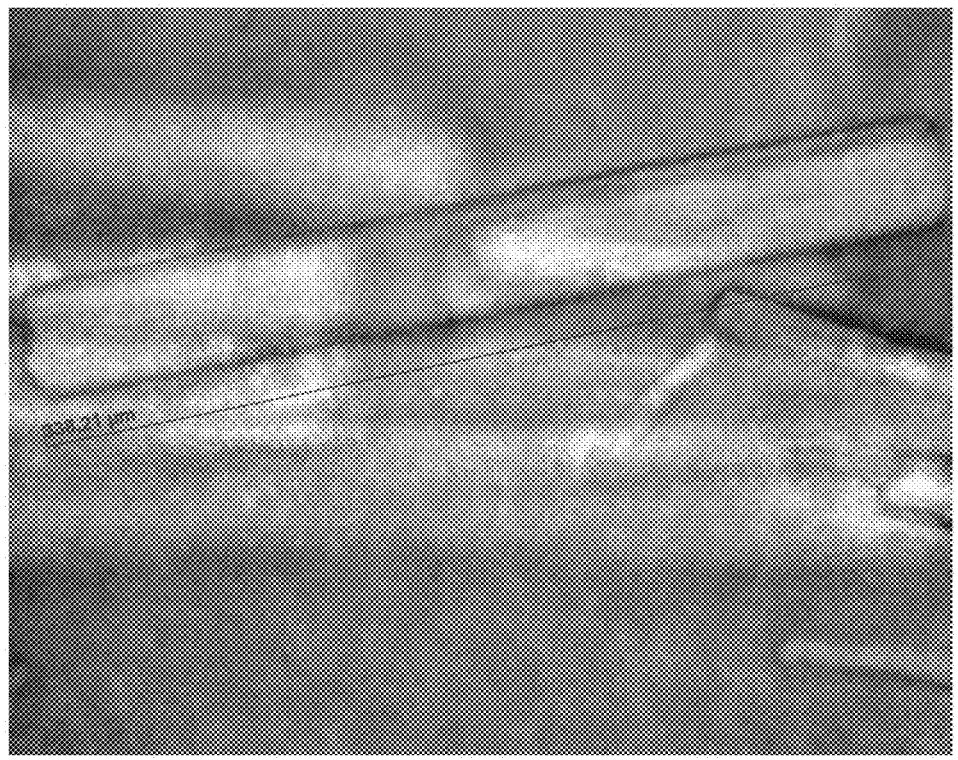
FIG. 2 shows a microscopic image of a single crystal, showing clearly the elongate shape of the crystal and a length along its long dimension in excess of 330 microns (338.21 microns)

The invention will be further illustrated with reference to the following examples.

EXAMPLE 1

Preparation of Homofarnesol
General Analytical Conditions:
Non-polar GC/MS: 50° C./2 min, 20° C./min 200° C., 35° C./min 270° C. GC/MS Agilent 5975C MSD with HP 7890A Series GC system. Non-polar column: BPX5 from SGE, 5% phenyl 95% dimethylpolysiloxane 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

A) Preparation of MNU in THF

A solution of urea (175 g, 2.9 mol) and methylamine hydrochloride (198 g, 2.9 mol) in water (400 ml) is heated at reflux (105° C.) for 3.5 h under stirring. At 40° C. $NaNO_2$ (101 g, 1.45 mol) dissolved in water (200 ml) is added. After 15 min THF (1000 ml) is added which results in a transparent 2-phase mixture. Conc. $H_2SO_4$ (110 g, 1.1 mol) is added at 0-5° C. and stirring within 1.5 h. After another 0.5 h at 0-5° C., the two transparent phases are separated at 25° C. The organic phase (A) (1065 ml, theoretically 1.35M) is stored for a few days at 0-5° C. or forwarded immediately to the cyclopropanation reactor.

After phase separation, the water phase is extracted twice with THF (2×1 l). This gives 1100 ml of phase B and 1075 of phase C. Whereas phase A gives a 51% conversion of a terminal alkene to a cyclopropane in a subsequent cyclopropanation reaction, phase B gives <0.5% cyclopropane and phase C gives no detectable conversion. We conclude that >99% MNU is extracted after the first phase separation. Usually the water phase is therefore discarded after the first phase separation (from organic phase A) after treatment with conc. aqueous KOH and acetic acid B) Preparation of E-Δ-Farnesene Using MNU in THF

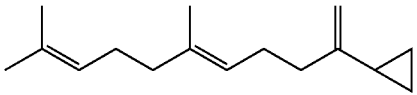 [SMILES: C=C(CC/C=C(\C)CCC=C(C)C)C1CC1]

N-Methyl-N-nitroso urea 1.35M in THF (136 ml, 184 mmol) is added dropwise at 0° C. to a rapidly stirred mixture of E-beta-Farnesene (CAS 18794-84-8) (25 g, 122 mmol) and aqueous KOH (50 ml, 40%) at 0-5° C. After the addition of 4 ml of the MNU solution, Pd(acac)$_2$ (7.4 mg, 0.024 mmol, 0.02%) pre-dissolved in 0.5 ml dichloromethane is added. The remaining MNU solution is added over 4 h at 0-5° C. A GC at this stage showed 28% unconverted E-beta-Farnesene, 65% of the desired monocyclopropane (shown above) and 3% of a biscyclopropanated compound 5. After 16 h at 25° C., acetic acid (100 ml) is added at 0-5° C., then tert-butyl methyl ether (250 ml). After phase separation the organic phase is washed with 2M HCl (250 ml) and the aqueous phase extracted with tert-butyl methyl ether (250 ml). The combined organic layers are washed with water (2×100 ml), aqueous 10% NaOH (2×100 ml) and water (2×100 ml), dried over MgSO$_4$, filtered and concentrated to give 26.9 g of a slightly yellow liquid which contains 9% E-beta-Farnesene, 82% of the desired monocyclopropane compound and 6% of a biscyclopropanated side product.

The desired compound could be further isolated by distillative purification.

Addition of 1 g K$_2$CO$_3$ (1 g) and distillation over a 30 cm steel coil column at 40-60 mbar gives 147 g monocyclopropane compound (68% corr) at 135-145° C. The fractions are pooled to give 92 g monocyclopropane compound of 100% purity.

Analytical Data of E-Δ Farnesene:

1H-NMR (CDCl$_3$, 400 MHz): 5.1 (2 m, 2H), 4.6 (2H), 2.2 (2H), 2.1 (4H), 2.0 (2H), 1.7 (s, 3H), 1.6 (2s, 6H), 1.3 (1H), 0.6 (2H), 0.45 (2H) ppm. 13C-NMR (CDCl$_3$, 400 MHz): 150.9 (s), 135.1 (s), 131.2 (s), 124.4 (d), 124.1 (d), 106.0 (t), 39.7 (t), 35.9 (t), 26.7 (t), 25.7 (q), 17.7 (q), 16.0 (d), 6.0 (t) ppm. GC/MS: 218 (2%, M+), 203 (5%, [M−15]+), 175 (11%), 147 (31%), 134 (15%), 133 (20%), 121 (12%), 107 (55%), 95 (16%), 93 (30%), 91 (20%), 82 (11%), 81 (33%), 79 (42%), 69 (100%), 67 (22%), 55 (20%), 53 (21%), 41 (75%). IR (film): 3081 (w), 2967 (m), 2915 (m), 2854 (m), 1642 (m), 1439 (m), 1377 (m), 1107 (w), 1047 (w), 1018 (m), 875 (s), 819 (m), 629 (w). Anal. calcd. for C$_{16}$H$_{26}$: C, 88.00; H, 12.00. Found: C, 87.80; H, 12.01.

C) Preparation of (7E)-4,8,12-trimethyltrideca-3,7,11-trien-1-ol ((7E)-homofarnesol)

A mixture of (E)-(6,10-dimethylundeca-1,5,9-trien-2-yl)cyclopropane (E-Δ Farnesene) (1 g, 4.6 mmol), dodecane (0.2 g, 1.15 mmol, internal standard) and L-(+)-tartaric acid (1 g, 6.9 mmol) in a pressure tube is heated under stirring at 150° C. After 18 h and complete conversion (according to GC), the mixture is poured on water (50 ml) and toluene (50 ml). The phases are separated and the aqueous phase extracted with toluene (50 ml). The combined organic layers are washed with conc. aqueous Na$_2$CO$_3$ (50 ml) and conc. NaCl (2×50 ml), dried over MgSO$_4$, filtered and evaporated under reduced pressure to give a brownish resin (1.35 g) which is mixed with 30% aqueous KOH (4.3 ml) and stirred at 25° C. for 2 h. GC analysis reveals formation of 96% (7E)-4,8,12-trimethyltrideca-3,7,11-trien-1-ol according to the internal standard. E/Z ratio 68:22. The analytical data of the E-isomer are consistent with the ones from the literature, see for example P. Kocienski, S. Wadman J. Org. Chem. 54, 1215 (1989).

EXAMPLE 2

SHC Plasmid Preparation and Biocatalyst Production
SHC Plasmid Preparation

The gene encoding *Alicyclobacillus acidocaldarius* squalene hopene cyclase (AacSHC) (GenBank M73834, Swissprot P33247) was inserted into plasmid pET-28a(+), where it is under the control of an IPTG inducible T7-promotor for protein production in *Escherichia coli*. The plasmid was transformed into *E. coli* strain BL21(DE3) using a standard heat-shock transformation protocol.

Erlenmeyer Flask Cultures

For protein production were used either rich medium (LB medium) or minimal media. M9 is one example of minimal media, which were successfully used.

Media Preparation

The minimal medium chosen as default was prepared as follows for 350 ml culture: to 35 ml citric acid/phosphate stock (133 g/l KH$_2$PO$_4$, 40 g/l (NH$_4$)$_2$HPO$_4$, 17 g/g citric acid.H$_2$O with pH adjusted to 6.3) was added 307 ml H$_2$O, the pH adjusted to 6.8 with 32% NaOH as required. After autoclaving 0.850 ml 50% MgSO$_4$, 0.035 ml trace elements solution (composition in next section) solution, 0.035 ml Thiamin solution and 7 ml 20% glucose were added.

SHC Biocatalyst Production (Biocatalyst Production)

Small scale biocatalyst production (wild-type SHC or SHC variants), 350 ml culture (medium supplemented with 50 µg/ml kanamycin) were inoculated from a pre-culture of the *E. coli* strain BL21(DE3) containing the SHC production plasmid. Cells were grown to an optical density of approximately 0.5 (OD$_{650\ nm}$) at 37° C. with constant agitation (250 rpm).

Protein production was then induced by the addition of IPTG to a concentration of 300 µM followed by incubation for a further 5-6 hours with constant shaking. The resulting bio-mass was finally collected by centrifugation, washed with 50 mM Tris-HCl buffer pH 7.5. The cells were stored as pellets at 4° C. or −20° C. until further use. In general 2.5 to 4 grams of cells (wet weight) were obtained from 1 litre of culture, independently of the medium used.

The fermentation was prepared and run in 750 ml InforsHT reactors. To the fermentation vessel was added 168 ml deionized water. The reaction vessel was equipped with all required probes (pO$_2$, pH, sampling, antifoam), C+N feed and sodium hydroxide bottles and autoclaved. After autoclaving, the following ingredients are added to the reactor:—

20 ml 10× phosphate/citric acid buffer
14 ml 50% glucose
0.53 ml MgSO$_4$ solution
2 ml (NH$_4$)$_2$SO$_4$ solution
0.020 ml trace elements solution
0.400 ml thiamine solution
0.200 ml kanamycin stock The reaction conditions are set as follows: pH=6.95, pO$_2$=40%, T=30° C., Stirring at 300 rpm. Cascade: rpm setpoint at 300, min 300, max 1000, flow l/min set point 0.1, min 0, max 0.6. Antifoam control: 1:9.

The fermenter was inoculated from a seed culture to an OD$_{650\ nm}$ of 0.4-0.5. This seed culture was grown in LB medium (+Kanamycin) at 37° C., 220 rpm for 8 h. The fermentation was run first in batch mode for 11.5 h, where after was started the C+N feed with a feed solution (sterilized glucose solution (143 ml H$_2$O+35 g glucose) to which had been added after sterilization: 17.5 ml (NH$_4$)$_2$SO$_4$ solution, 1.8 ml MgSO$_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approximately 25 hours, where they reached typically and $OD_{650\,nm}$ of 40-45. SHC production was then started by adding IPTG to a final concentration of approx. 1 mM in the fermenter (as IPTG pulse or over a period of 3-4 hours using an infusion syringe), setting the temperature to 40° C. and $pO_2$ to 20%. Induction of SHC production lasted for 16 h at 40° C. At the end of induction the cells were collected by centrifugation, washed with 0.1M citric acid/sodium citrate buffer pH 5.4 and stored as pellets at 4° C. or −20° C. until further use.

Results Ia

In general, with all other conditions unchanged the specific activity of the produced biocatalyst was higher when a minimal medium was used compared with a rich medium.

Induction was carried out successfully at 30 or 37° C. It was noted that when the induction was done at 40-43° C., a biocatalyst of higher specific activity was obtained.

Results Ib

The following Table 1 shows for two examples the culture volume, optical density and amount of cells both at induction start and induction end as well as the amount of biomass collected (wet weight).

TABLE 1

| | Volume induction start (ml) | $OD_{650\,nm}$ induction start | cells calculated (g) | Volume induction end (ml) | $OD_{650\,nm}$ induction end | cells collected (g) |
|---|---|---|---|---|---|---|
| Example 1 | 273 | 40 | 10.9 | 342 | 55 | 28 |
| Example 2 | 272 | 44 | 12.0 | 341 | 57 | 23 |

$OD_{650\,nm}$ at inoculation: 0.45 (Example 1) and 0.40 (Example 2). Starting volumes: 205 ml.

Wild Type SHC Amino Acid Sequence (SEQ ID No. 1) (GenBank M73834 Swissprot P33247)

MAEQLVEAPAYARTLDRAVEYLLSCQKDEGYWWGPLLSNVTMEAEYVLLC

HILDRVDRDRMEKIRRYLLHEQREDGTWALYPGGPPDLDTTIEAYVALKY

IGMSRDEEPMQKALRFIQSQGGIESSRVFTRMWLALVGEYPWEKVPMVPP

EIMFLGKRMPLNIYEFGSWARATVVALSIVMSRQPVFPLPERARVPELYE

TDVPPRRRGAKGGGGWIFDALDRALHGYQKLSVHPFRRAAEIRALDWLLE

RQAGDGSWGGIQPPWFYALIALKILDMTQHPAFIKGWEGLELYGVELDYG

GWMFQASISPVWDTGLAVLALRAAGLPADHDRLVKAGEWLLDRQITVPGD

WAVKRPNLKPGGFAFQFDNVYYPDVDDTAVVVWALNTLRLPDERRRRDAM

TKGFRWIVGMQSSNGGWGAYDVDNTSDLPNHIPFCDFGEVTDPPSEDVTA

HVLECFGSFGYDDAWKVIRRAVEYLKREQKPDGSWFGRWGVNYLYGTGAV

VSALKAVGIDTREPYIQKALDWVEQHQNPDGGWGEDCRSYEDPAYAGKGA

STPSQTAWALMALIAGGRAESEAARRGVQYLVETQRPDGGWDEPYYTGTG

FPGDFYLGYTMYRHVFPTLALGRYKQAIERR

Variant F601Y SHC Amino Acid Sequence (SEQ ID No. 2)—Variant with Respect to SEQ ID No. 1

MAEQLVEAPAYARTLDRAVEYLLSCQKDEGYWWGPLLSNVTMEAEYVLLC

HILDRVDRDRMEKIRRYLLHEQREDGTWALYPGGPPDLDTTIEAYVALKY

IGMSRDEEPMQKALRFIQSQGGIESSRVFTRMWLALVGEYPWEKVPMVPP

EIMFLGKRMPLNIYEFGSWARATVVALSIVMSRQPVFPLPERARVPELYE

TDVPPRRRGAKGGGGWIFDALDRALHGYQKLSVHPFRRAAEIRALDWLLE

RQAGDGSWGGIQPPWFYALIALKILDMTQHPAFIKGWEGLELYGVELDYG

GWMFQASISPVWDTGLAVLALRAAGLPADHDRLVKAGEWLLDRQITVPGD

WAVKRPNLKPGGFAFQFDNVYYPDVDDTAVVVWALNTLRLPDERRRRDAM

TKGFRWIVGMQSSNGGWGAYDVDNTSDLPNHIPFCDFGEVTDPPSEDVTA

HVLECFGSFGYDDAWKVIRRAVEYLKREQKPDGSWFGRWGVNYLYGTGAV

VSALKAVGIDTREPYIQKALDWVEQHQNPDGGWGEDCRSYEDPAYAGKGA

STPSQTAWALMALIAGGRAESEAARRGVQYLVETQRPDGGWDEPYYTGTG

YPGDFYLGYTMYRHVFPTLALGRYKQAIERR

Variant F605W SHC Nucleotide Sequence (SEQ ID No. 3)

ATGGCTGAGCAGTTGGTGGAAGCGCCGGCCTACGCGCGGACGCTGGATCG

CGCGGTGGAGTATCTCCTCTCCTGCCAAAAGGACGAAGGCTACTGGTGGG

GGCCGCTTCTGAGCAACGTCACGATGGAAGCGGAGTACGTCCTCTTGTGC

CACATTCTCGATCGCGTCGATCGGGATCGCATGGAGAAGATCCGGCGGTA

CCTGTTGCACGAGCAGCGCGAGGACGGCACGTGGGCCCTGTACCCGGGTG

GGCCGCCGGACCTCGACACGACCATCGAGGCGTACGTCGCGCTCAAGTAT

ATCGGCATGTCGCGCGACGAGGAGCCGATGCAGAAGGCGCTCCGGTTCAT

TCAGAGCCAGGGCGGGATCGAGTCGTCGCGCGTGTTCACGCGGATGTGGC

TGGCGCTGGTGGGAGAATATCCGTGGGAGAAGGTGCCCATGGTCCCGCCG

GAGATCATGTTCCTCGGCAAGCGCATGCCGCTCAACATCTACGAGTTTGG

CTCGTGGGCTCGGGCGACCGTCGTGGCGCTCTCGATTGTGATGAGCCGCC

AGCCGGTGTTCCCGCTGCCCGAGCGGGCGCGCGTGCCCGAGCTGTACGAG

ACCGACGTGCCTCCGCGCGGGCGCGGTGCCAAGGGAGGGGGTGGGTGGAT

CTTCGACGCGCTCGACCGGGCGCTGCACGGGTATCAGAAGCTGTCGGTGC

ACCCGTTCCGCCGCGCGGCCGAGATCCGCGCCTTGGACTGGTTGCTCGAG

CGCCAGGCCGGAGACGGCAGCTGGGGCGGGATTCAGCCGCCTTGGTTTTA

CGCGCTCATCGCGCTCAAGATTCTCGACATGACGCAGCATCCGGCGTTCA

TCAAGGGCTGGGAAGGTCTAGAGCTGTACGGCGTGGAGCTGGATTACGGA

GGATGGATGTTTCAGGCTTCCATCTCGCCGGTGTGGGACACGGGCCTCGC

CGTGCTCGCGCTGCGCGCTGCGGGGCTTCCGGCCGATCACGACCGCTTGG

TCAAGGCGGGCGAGTGGCTGTTGGACCGGCAGATCACGGTTCCGGGCGAC

TGGGCGGTGAAGCGCCCGAACCTCAAGCCGGGCGGGTTCGCGTTCCAGTT

CGACAACGTGTACTACCCGGACGTGGACGACACGGCCGTCGTGGTGTGGG

CGCTCAACACCCTGCGCTTGCCGGACGAGCGCCGCAGGCGGGACGCCATG

-continued
ACGAAGGGATTCCGCTGGATTGTCGGCATGCAGAGCTCGAACGGCGGTTG

GGGCGCCTACGACGTCGACAACACGAGCGATCTCCCGAACCACATCCCGT

TCTGCGACTTCGGCGAAGTGACCGATCCGCCGTCAGAGGACGTCACCGCC

CACGTGCTCGAGTGTTTCGGCAGCTTCGGGTACGATGACGGCTGGAAGGT

CATCCGGCGCGCGGTGGAATATCTCAAGCGGaAGCAGAAGCCGGACGGCA

GCTGGTTCGGTCGTTGGGGCGTCAATTACCTCTACGGCACGGGCGCGGTG

GTGTCGGCGCTGAAGGCGGTCGGGATCGACACGCGCGAGCCGTACATTCA

AAAGGCGCTCGACTGGGTCGAGCAGCATCAGAACCCGGACGGCGGCTGGG

GCGAGGACTGCCGCTCGTACGAGGATCCGGCGTACGCGGGTAAGGGCGCG

AGCACCCCGTCGCAGACGGCCTGGGCGCTGATGGCGCTCATCGCGGGCGG

CAGGGCGGAGTCCGAGGCCGCGCGCCGCGGCGTGCAATACCTCGTGGAGA

CGCAGCGCCCGGACGGCGGCTGGGATGAGCCGTACTACACCGGCACGGGC

TTCCCAGGGGATTGGTACCTCGGCTACACCATGTACCGCCACGTGTTTCC

GACGCTCGCGCTCGGCCGCTACAAGCAAGCCATCGAGCGCAGGTGA

Variant F605W SHC Amino Acid Sequence (SEQ ID No. 4)—Variant with Respect to SEQ ID No. 1

MAEQLVEAPAYARTLDRAVEYLLSCQKDEGYWWGPLLSNVTMEAEYVLLC

HILDRVDRDRMEKIRRYLLHEQREDGTWALYPGGPPDLDTTIEAYVALKY

IGMSRDEEPMQKALRFIQSQGGIESSRVFTRMWLALVGEYPWEKVPMVPP

EIMFLGKRMPLNIYEFGSWARATVVALSIVMSRQPVFPLPERARVPELYE

TDVPPRRRGAKGGGGWIFDALDRALHGYQKLSVHPFRRAAEIRALDWLLE

RQAGDGSWGGIQPPWFYALIALKILDMTQHPAFIKGWEGLELYGVELDYG

GWMFQASISPVWDTGLAVLALRAAGLPADHDRLVKAGEWLLDRQITVPGD

WAVKRPNLKPGGFAFQFDNVYYPDVDDTAVVVWALNTLRLPDERRRDAM

TKGFRWIVGMQSSNGGWGAYDVDNTSDLPNHIPFCDFGEVTDPPSEDVTA

HVLECFGSFGYDDAWKVIRRAVEYLKREQKPDGSWFGRWGVNYLYGTGAV

VSALKAVGIDTREPYIQKALDWVEQHQNPDGGWGEDCRSYEDPAYAGKGA

STPSQTAWALMALIAGGRAESEAARRGVQYLVETQRPDGGWDEPYYTGTG

FPGDWYLGYTMYRHVFPTLALGRYKQAIERR

EXAMPLE 3A

Bioconversion of 7E, 3E/Z-Homofarnesol Mixture

Bioconversion was undertaken using the following reaction conditions:

The reaction (150.1 g total volume) run in 0.1M citric acid/sodium citrate buffer pH 5.4 in an InforsHT 750 ml fermenter contained 146 g/l total homofarnesol using a homofarnesol substrate, which was a mixture of 7E,3E:7E, 3Z of 86:14, 250 g/l cells (formed in accordance with the method of Example 2, fermentation) and 1.55% SDS. The reaction was run at 35° C. with constant stirring (900 rpm), pH control was done using 10 to 40% citric acid in water.

The reaction mixture was subjected to isolation and purification steps as set forth in Example 4, below.

EXAMPLE 3B

Bioconversion of 7E, 3E/Z-Homofarnesol Mixture

Bioconversion was undertaken using the following reaction conditions:

A reaction (2.5 ml total volume) was run with vigorous shaking (800 rpm) at 50° C. and pH 6.0 in 0.1M citric acid/sodium citrate buffer in a 11 ml a glass reaction vessel on an Heidolph Synthesis 1 apparatus. The reaction contained 1 g/l E,E-Homofarnesol (from a Homofanesol stock of EE:EZ ratio of 86:14), cells that had produced the wild type SHC enzyme in accordance with the method described in Example 2 to an $OD_{650\ nm}$ of 30 and 0.12% SDS. About 48 h after reaction start was E,E-Homofarnesol conversion about 60%. When the reaction was cooled down to room temperature, Ambrofix crystals appeared upon microscopic analysis of a sample taken from the reaction mixture. A further addition of cells equivalent to an in increase in $OD_{650\ nm}$ by 10 and further incubation for 24 hours allowed complete E,E-Homofarnesol conversion. Microscopic observation of a sample of the reaction mixture indicated the presence of an increased number of Ambrofix crystals.

The reaction was also run in an InforsHT 750 ml fermenter in 150.1 g total volume at pH 6.0 in 0.1M citric acid/sodium citrate buffer. The reaction contained 1 g/l E,E-Homofarnesol, 0.12% SDS and cells that had produced wild type SHC at 118 g/l wet weight and was incubated at 50° C. with vigorous shaking (700 rpm). Approximately 30 hours after reaction start was E,E-Homofarnesol conversion approximately 85%. Microscopic observation of a sample of the reaction mixture allowed identification of Ambrofix crystals. Homofarnesol was added again to an equivalent of 1 g/l and the reaction run for an additional approx. 50 hours; cells were added as well to the equivalent of 32 g/l (wet weight). About 66 hours total reaction time was E,E-Homofarnesol conversion approximately 85%. Microscopic observation of the reaction mixture allowed the observation of an increased number of Ambrox crystals.

EXAMPLE 4

Figure 4:
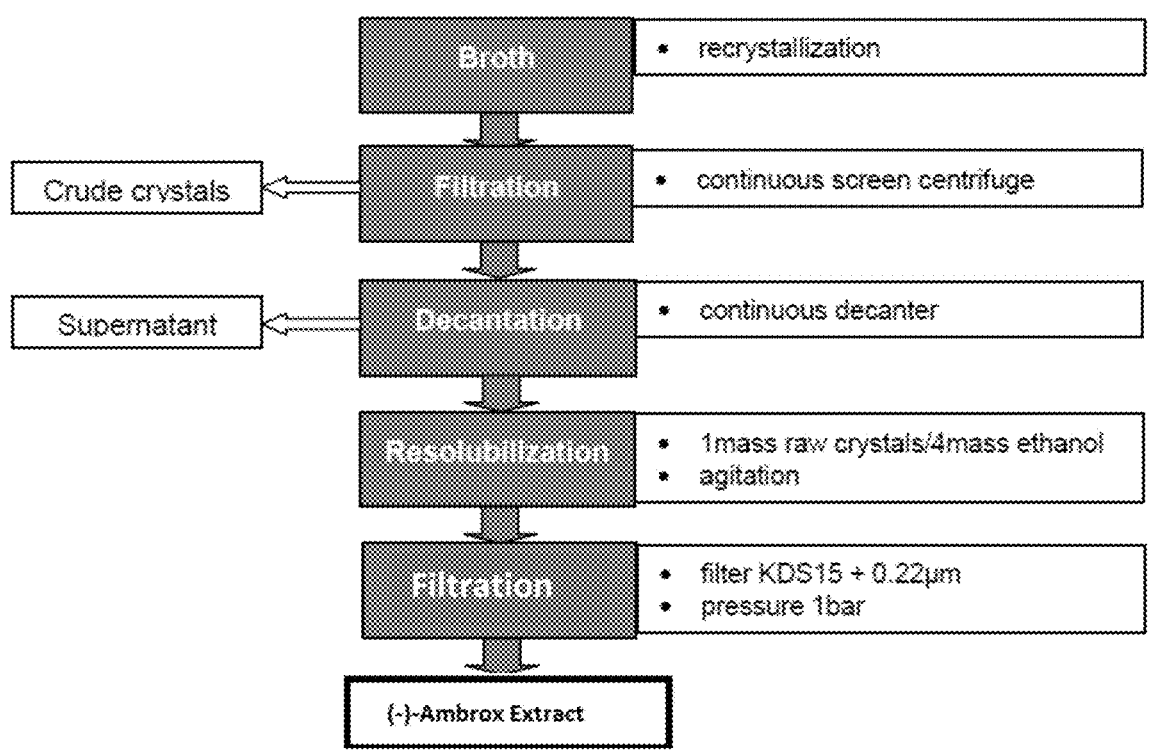
FIG. 4 shows an outline of a down-stream process to produce (−)-Ambrox. The (−)-Ambrox extract obtained can be subjected to further deodorizing or decolourizing steps as described in more detail herein below.

A general down-stream process is set forth in FIG. 4, below, for reference.

In a first step, the bioconversion medium is heated to a temperature of about 80 to 85° C. for a period of about 15 minutes, melting the crystals of (−)-Ambrox The (−)-Ambrox, which is liquid at this stage is recrystallized by cooling the reaction medium to a temperature of 20° C. at a rate of about 5° C. per hour.

In a second step, after (−)-Ambrox has crystallized, the crystals are separated from the bioconversion medium by filtration. Filtration is carried out in a continuous screen centrifuge (Siebtechnic H250) with a sieve size 100 microns. The centrifuge is operated at an acceleration of 2028 G, and a feed rate of 430 kg/hour. Owing to the significant size difference between crystals and cell debris, most of the crystals are retained on the sieve, and can be washed with water and collected mechanically by means of a knife provided for such a purpose.

In a third step, the filtrate from the second step is fed into a continuous decanter set up to separate cell debris, retained in the supernatant, from any crystals that passed through the filter in step 2, which settle in the decanter apparatus as a sediment. The decanter is operated at 1170 G and a feed rate of 370 kg/hour. The crystals collected in the decanter are washed with water, and combined with the crystals obtained in step 2. The combined crystals are washed and decanted statically to remove any residual cell debris in the supernatant, and the washed crystals are ready for further processing.

In a fourth step, the washed crystals are re-solubilized with ethanol (96% technical grade) in an amount of 1 mass crystals to 4 mass ethanol. The solution is filtered over a sub-micron filter (0.6 to 1.0 micron, KDS15) at ambient temperature and 1 bar pressure, before being filtered again through a 0.22 micron filter.

The (−)-Ambrofix extract thus formed can be subjected to further deodourizing and decolouration steps, as follows.

The ethanolic solution was concentrated to dryness under vacuum. The concentrate was re-dissolved in industrial grade denatured ethanol and a bleaching agent (Tonsil 412FF) plus a diatomaceous earth filter agent (CELATOM FW 50) were added under stirring. The mixture was refluxed at 80-85° C. under stirring for 30 minutes, before cooling to 55-60° C. The mixture was filtered over a 25 micron filter to remove the solid materials.

Excess denatured alcohol was eliminated from the clear bleached solution by atmospheric pressure distillation. Water was then fed to the hot solution and the resulting mixture agitated for 15 minutes at 75-80° C. The (−)-Ambrox was crystallized by gradually cooling this solution down to −10 to −15° C. The crystallized (−)-Ambrox was filtered off and dried in a vacuum oven (50-60° C.; 1-5 mbar).

EXAMPLE 5A

Figure 3:
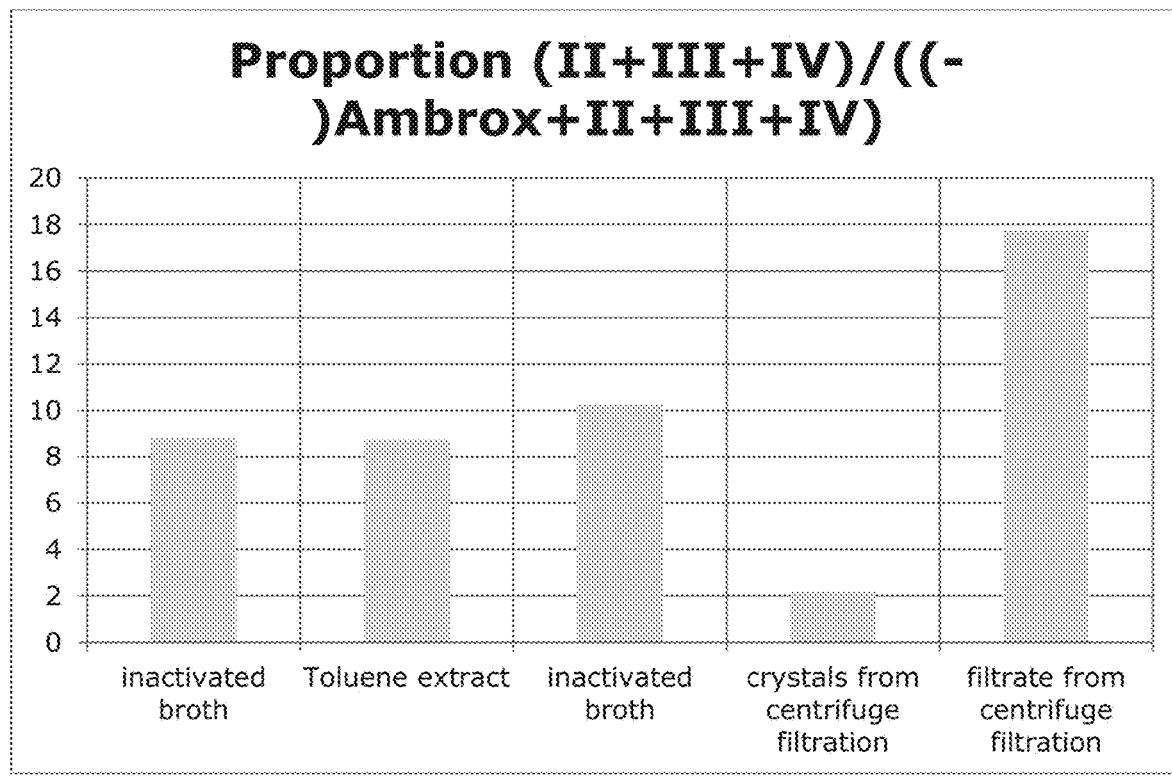
FIG. 3 compares the relative amounts of (−)-Ambrox and its isomers (II), (III) and (IV) in a bioconversion medium; a toluene extract; the crystal form; and the filtrate after crystal collection.

Down Stream Processing: Comparison of Solid-Liquid Separation and Toluene Extraction as a Means of Selectively Isolating (−)-Ambrox from the Bioconversion Medium 200 ml of inactivated bioconversion medium was extracted with MTBE and analyzed by gas chromatography.
Solid-Liquid Separation 200 ml of inactivated bioconversion medium was centrifuged to separate the solid from the liquid phase (Sorvall GS3, 5000 rpm, 10 min, 10° C.). This separated approx. 80 ml solid pellet from approx. a 120 ml liquid supernatant. The supernatant was removed, extracted with MTBE and analyzed by gas chromatography. Similarly, the pellet was extracted with MTBE and the MTBE extract analyzed by gas chromatography.
Toluene Extraction 200 ml of bioconversion medium was extracted with 6× 45 ml toluene. The organic phase was collected and filtered to remove any cell debris. Toluene was stripped off, and the residue dissolved in MTBE, before being analyzed by gas chromatography.
Analysis The GC analysis results are depicted in FIG. 3, below. From the results it is clear that the The solid phase collected by centrifuge contained very high levels of (−)-Ambrox, and very low amounts of by-products II, III and IV. On the other hand, the toluene extract was not enriched in (−)-Ambrox compared with the crude bioconversion medium. The results indicate that whereas (−)-Ambrox crystallizes from the bioconversion medium; the structurally related compounds (II), (III) and (IV) remain in the liquid phase. The residues of (II), (III) and (IV) that were found in the analysis of the solid phase were merely residues that could be removed with a thorough washing of the solid phase. One can conclude from this experiment that not only does a particle size separation step (such as filtration and/or decantation) allow separation of a solid form of (−)-Ambrox from cell debris, it also can be used to entirely or substantially separate solid (−)-Ambrox from structurally related by-products, such as compounds (II), (III) and (IV).

EXAMPLE 5B

Sensory Analysis

Purpose: To Carry Out a Sensory Analysis of (−)-Ambrox and the Compounds (II), (III) and (IV) Formed in the Crude Material and in the Crystallised Material.

Biotransformation of E,E-homofarnesol results in (−)-Ambrox, and compound (IV).

Biotransformation of E,Z-homofarnesol results in the macrocyclic ether compound (II) and epi-Ambrox compound (III).

A crude mixture of (−)-Ambrox comprises the desired (−)-Ambrox, compound (II), (III) and (IV) present in an amount of 87.1 wt %, 2.8 wt %, 2.5 wt % and 7.6 wt % respectively.

When a crude mixture is selectively crystallised (lab scale), the crystallised material, when analyzed by gas chromatography has the same components as the crude mixture, but they are present in an amount of 99.1 wt %, 0.1 wt %, 0.1 wt % and 0.7 wt % respectively. The residues of (II), (III) and (IV) are believed to by oily residues attached to crystals of (−)-Ambrox.

The Sensory Analytical Results were as follows:

(−)-Ambrox: Odour Threshold 0.2 ng/l.

Compound (IV): weak, IsoE, woody, GC-detection threshold 5-10 ng.

Compound (II): "odorless" (GC-threshold >500 ng).

Compound (III): GC-threshold about 10× higher than (−)-Ambrox (circa 2 ng).

The sensory analysis of the 3 by-products (compounds II, III and IV) indicates a weaker odour than that from (−)-Ambrox. In fact, the epi-Ambrox (Compound III) odor is about 10 fold weaker than (−)-Ambrox suggesting that it is essentially odorless.

The sensory analysis demonstrated that the removal of one of more by-product compounds from (−)-Ambrox can improve the odor of the remaining compound (i.e. ( ) Ambrox) even if the removed compounds are actually odorless compounds per se. That is, an Ambrox odor enhancement in terms of olfactive purity as determined by trained Perfumers (using recognised benchmarks for acceptable olfactive purity) was observed in the absence of compounds II, III and IV.

EXAMPLE 6

X-Ray Characterization of the Solid Form of (−) Ambrox Formed by the Microbial Fermentation Process Powder X-ray diffraction patterns were acquired using a STOE STADI P X-ray diffractometer.

System description: The diffractometer was used in transmission mode (flat sample holders, curved Germanium (111) monochromator, and CuKa1 radiation 1.54060 Angstrom) by using a position-sensitive detector. The generator Voltage was 40 kV and the current 40 mA. The detector: Mythen 1K.

Experimental parameters: Pattern measurement was made between 2 theta=about 4° to 26°. The accuracy of the diffraction angles determined is approximately +/−0.2° 2 theta.

The invention claimed is:

1. A method of preparing a solid form of (−)-Ambrox of the formula (I)

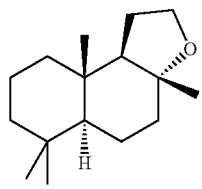

wherein, said solid form is characterized by at least one of the following characteristics:
- it exhibits an x-ray diffraction pattern having at least one of the following peaks at diffraction angles 2 theta of 15.6, 16.2, 16.7, 17.0, 17.4, 18.3 +/−0.2°;
- it comprises elongate crystals having an average diameter of at least 10 to 400 microns measured by laser granulometry;
- it comprises elongate crystals having a length along their longest dimension of greater than 100 micron; and/or
- it has an L* value of 90 or more; an a* value of less than 1 and greater the −1; and a b* value, which is less than 8, wherein L*, a* and b* values represent CIELAB L*a*b* chromaticity coordinates, wherein the solid form of (−)-Ambrox is formed by a bioconversion process, said method comprising the steps of:
I) forming crystalline (−)-Ambrox in a bioconversion medium by means of a biocatalytic process; and
II) separating the crystalline (−)-Ambrox from the bioconversion medium.

2. The method according to claim 1, wherein the separation step is a filtration step, a decantation step, or a combination of both a filtration step and a decantation step.

3. The method according to claim 1, wherein prior to the separation step, the bioconversion medium is heated to a temperature of at least 80° C. to melt the crystalline (−)-Ambrox; and thereafter slowly cooled in order that the (−)-Ambrox is recrystallized from the bioconversion medium.

4. The method according to claim 1, wherein the recovered crystals of (−)-Ambrox are solubilized in a solvent, and the solution filtered through a sub-micron filter to remove any residual particulate material that was present in the bioconversion medium, before being rendered in solid form by removing the solvent by evaporation or recrystallization.

5. The method according to claim 1, wherein the bioconversion process is an enzyme-catalyzed cyclization of homofarnesol comprising a mixture of 7E,3E and 7E,3Z geometric isomers of homofarnesol, wherein the reaction is carried out in the presence of a biocatalyst, and wherein the biocatalyst is a recombinant microorganism expressing the gene coding the enzyme, or an isolated enzyme, or an immobilized enzyme.

6. The method according to claim 5, wherein the enzyme is a wild-type squalene hopene cyclase, or a variant of the wild-type squalene hopene cyclase.

7. The method according to claim 1, wherein the crystals are washed with water, water-miscible solvents or mixtures thereof.

8. The method according to claim 1, wherein recovery of the (−)-Ambrox is achieved by its mechanical removal from a filter or decanter apparatus or belt filter, collection and drying.

9. The method according to claim 4, wherein the solution of the solubilised (−)-Ambrox crystals is contacted with a bleaching agent.

* * * * *

SEQUENCE LISTING

<160> NUMBER OF SEQ ID NOS: 4

<210> SEQ ID NO 1
<211> LENGTH: 631
<212> TYPE: PRT
<213> ORGANISM: Alicyclobacillus acidocaldarius

<400> SEQUENCE: 1

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

-continued

Asn Val Tyr Tyr Pro Asp Val Asp Asp Thr Ala Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
                435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
    515                 520                 525

Pro Asp Gly Gly Trp Gly Glu Asp Cys Arg Ser Tyr Glu Asp Pro Ala
530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Phe Tyr Leu Gly
    595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 2
<211> LENGTH: 631
<212> TYPE: PRT
<213> ORGANISM: Artificial sequence
<220> FEATURE:
<223> OTHER INFORMATION: Synthetic AacSHC Derivative

<400> SEQUENCE: 2

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
        50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

-continued

```
Ala Leu Lys Tyr Ile Gly Met Ser Arg Asp Glu Pro Met Gln Lys
                100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Arg Arg Arg
        195                 200                 205

Gly Ala Lys Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
```

```
                    515                 520                 525
Pro Asp Gly Gly Trp Gly Glu Asp Cys Arg Ser Tyr Glu Asp Pro Ala
            530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Tyr Pro Gly Asp Phe Tyr Leu Gly
                595                 600                 605

Tyr Thr Met Tyr Arg His Val Phe Pro Thr Leu Ala Leu Gly Arg Tyr
            610                 615                 620

Lys Gln Ala Ile Glu Arg Arg
625                 630

<210> SEQ ID NO 3
<211> LENGTH: 1896
<212> TYPE: DNA
<213> ORGANISM: Artificial sequence
<220> FEATURE:
<223> OTHER INFORMATION: Synthetic AacSHC Derivative

<400> SEQUENCE: 3
atggctgagc agttggtgga agcgccggcc tacgcgcgga cgctggatcg cgcggtggag      60
tatctcctct cctgccaaaa ggacgaaggc tactggtggg gccgcttct gagcaacgtc     120 acgatggaag cggagtacgt cctcttgtgc acattctcg atcgcgtcga tcgggatcgc     180
atggagaaga tccggcggta cctgttgcac gagcagcgcg aggacggcac gtgggccctg     240
tacccgggtg ggccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa gcgcatgccg     480
ctcaacatct acgagtttgg ctcgtgggct cgggcgaccg tcgtggcgct tcgattgtg     540 atgagccgcc agccggtgtt cccgctgccc gagcgggcgc gcgtgcccga gctgtacgag     600
accgacgtgc tccgcgccg gcgcggtgcc aaggagggg gtgggtggat cttcgacgcg     660
ctcgaccggg cgctgcacgg gtatcagaag ctgtcggtgc acccgttccg ccgcgcggcc     720
gagatccgcg ccttggactg gttgctcgag cgccaggccg agacggcag ctggggcggg     780 attcagccgc cttggtttta cgcgctcatc gcgctcaaga ttctcgacat gacgcagcat     840
ccggcgttca tcaagggctg gaaggtctca gagctgtacg cgtggagct ggattacgga     900 ggatggatgt tcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat ccgctggat tgtcggcatg cagagctcga acggcggttg gggcgcctac    1260
gacgtcgaca cacgagcga tctcccgaac cacatcccgt tctgcgactt cggcgaagtg    1320
accgatccgc cgtcagagga cgtcaccgcc cacgtgctcg agtgtttcgg cagcttcggg    1380
```

```
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacggc ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg attggtacct cggctacacc atgtaccgcc acgtgtttcc gacgctcgcg    1860
ctcggccgct acaagcaagc catcgagcgc aggtga                              1896

<210> SEQ ID NO 4
<211> LENGTH: 631
<212> TYPE: PRT
<213> ORGANISM: Artificial sequence
<220> FEATURE:
<223> OTHER INFORMATION: Synthetic AacSHC Derivative

<400> SEQUENCE: 4

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270
```

-continued

```
Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
        290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Trp Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```